US011944935B2

(12) United States Patent
Mou et al.

(10) Patent No.: US 11,944,935 B2
(45) Date of Patent: Apr. 2, 2024

(54) GAS DETECTION PURIFICATION DEVICE

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Chang-Yen Tsai, Hsinchu (TW); Wei-Ming Lee, Hsinchu (TW); Tsung-I Lin, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 732 days.

(21) Appl. No.: 17/109,370

(22) Filed: Dec. 2, 2020

(65) Prior Publication Data

US 2021/0220773 A1 Jul. 22, 2021

(30) Foreign Application Priority Data

Jan. 16, 2020 (TW) ................................ 109101604

(51) Int. Cl.

| | |
|---|---|
| ***A61L 9/00*** | (2006.01) |
| ***B01D 53/75*** | (2006.01) |
| ***B03C 3/01*** | (2006.01) |
| ***F24F 8/10*** | (2021.01) |
| ***F24F 8/158*** | (2021.01) |
| ***F24F 8/192*** | (2021.01) |

(Continued)

(52) U.S. Cl.

CPC ................ *B01D 53/75* (2013.01); *F24F 8/10* (2021.01); *F24F 8/158* (2021.01); *F24F 8/192* (2021.01); *F24F 8/22* (2021.01); *F24F 8/80* (2021.01); *F24F 8/95* (2021.01); *F24F 11/72* (2018.01); *G01N 33/0004* (2013.01); *F24F 2110/66* (2018.01)

(58) Field of Classification Search

CPC ..... B01D 46/0079; F02M 35/086; A62D 9/00
USPC .............................. 422/305–306; 96/55, 397
See application file for complete search history.

(56) References Cited

U.S. PATENT DOCUMENTS

| | | | |
|---|---|---|---|
| 7,419,533 | B2 | 9/2008 | Son et al. |
| 2015/0343361 | A1 | 12/2015 | Holzmann et al. |

FOREIGN PATENT DOCUMENTS

| | | | |
|---|---|---|---|
| CN | 205174708 | U | 4/2016 |
| CN | 209089775 | U | 7/2019 |

(Continued)

*Primary Examiner* — Monzer R Chorbaji
(74) *Attorney, Agent, or Firm* — Birch, Stewart, Kolasch & Birch, LLP

(57) ABSTRACT

A gas detection purification device is disclosed and includes a main body, a purification unit, a gas guider, a gas detection module and a controlling-driving module. The main body includes an inlet, an outlet, an external socket and a gas-flow channel disposed between the inlet and the outlet. The purification unit is disposed in the gas-flow channel for filtering gas introduced through the gas-flow channel. The gas guider is disposed in the gas channel and located at a side of the purification unit. The gas is inhaled through the inlet, flows through the purification unit and is discharged out through the outlet. The gas detection module is plugged into or detached from the external socket. The controlling driving module is disposed within the main body and electrically connected to the gas guider to control the operation of the gas guider in an enabled state and a disabled state.

18 Claims, 34 Drawing Sheets

(51) Int. Cl.

| | |
|---|---|
| ***F24F 8/22*** | (2021.01) |
| ***F24F 8/80*** | (2021.01) |
| ***F24F 8/95*** | (2021.01) |
| ***F24F 11/72*** | (2018.01) |
| ***G01N 33/00*** | (2006.01) |
| *F24F 110/66* | (2018.01) |

(56) References Cited

FOREIGN PATENT DOCUMENTS

| | | | | | |
|---|---|---|---|---|---|
| CN | 209089776 | U | | 7/2019 | |
| CN | 209188372 | U | | 8/2019 | |
| CN | 110501454 | A | | 11/2019 | |
| CN | 209809754 | U | * | 12/2019 | ............. G01N 15/06 |
| CN | 209809754 | U | | 12/2019 | |
| TW | M415274 | U1 | | 11/2011 | |
| TW | M509328 | U | | 9/2015 | |
| TW | I572830 | B | | 3/2017 | |
| TW | M547670 | U | | 8/2017 | |
| TW | M558635 | U | | 4/2018 | |
| TW | M567364 | U | | 9/2018 | |
| TW | M581748 | U | | 8/2019 | |

* cited by examiner

4b 4b
46
414
414b
45
416
415a
416b
42

GAS DETECTION PURIFICATION DEVICE

CROSS-REFERENCE TO RELATED APPLICATION

This application aims the priority to Taiwanese Application No. 109101604 filed Jan. 16, 2020 and entitled "GAS DETECTION PURIFICATION DEVICE", the entire contents of which are incorporated herein by reference for all purposes.

FIELD OF THE INVENTION

The present disclosure relates to a gas detection purification device, and more particularly to a gas detection purification device implemented in an indoor space.

BACKGROUND OF THE INVENTION

In recent, people pay more and more attention to the quality of the air around their lives. For example, carbon monoxide, carbon dioxide, volatile organic compounds (VOC), PM2.5, nitric oxide, sulfur monoxide and even the suspended particles contained in the air are exposed in the environment to affect the human health, and even endanger the life seriously. Therefore, the quality of environmental air has attracted the attention of various countries. At present, how to detect the air quality and avoid the harm is a problem that urgently needs to be solved.

In order to confirm the quality of the air, it is feasible to use a gas sensor to detect the air surrounding in the environment. If the detection information is provided in real time to warn the people in the environment, it is helpful of avoiding the harm and facilitates the people to escape the hazard immediately. Thus, it prevents the hazardous gas exposed in the environment from affecting the human health and causing the harm. Therefore, it is a very good application to use a gas sensor to detect the air in the surrounding environment. On the other hand, the gas purification device is an air-pollution solution for modern people to prevent inhalation of the hazardous gas. Therefore, how to combine the gas purification device and the gas sensor, detect the air quality in real time, anytime, anywhere, and provide the benefits of purifying the air quality is a main subject developed in the present disclosure.

SUMMARY OF THE INVENTION

An object of the present disclosure provides a gas detection purification device. With an external pluggable or detachable gas detection module embedded in the gas purification device, air quality around the gas purification device is detected at any time, and information of the air quality is transmitted to an external device in real time to obtain gas detection information and an alarm notice. It prevents the hazardous gas exposed in the environment from affecting the human health and causing the harm. Furthermore, the gas purification device is utilized to provide the benefits of purifying the air quality.

In accordance with an aspect of the present disclosure, a gas detection purification device is provided and includes a main body, a purification unit, a gas guider, a gas detection module and a controlling-driving module. The main body includes at least one inlet, at least one outlet, a gas-flow channel and an external socket. The gas-flow channel is disposed between the at least one inlet and the at least one outlet. The purification unit is disposed in the gas-flow channel for filtering gas introduced through the gas-flow channel. The gas guider is disposed in the gas-flow channel and located at a side of the purification unit. The gas is inhaled through the at least one inlet, flows through the purification unit for filtration and purification, and is discharged out through the at least one outlet. The gas detection module is plugged into the external socket and integrally connected to the main body as one piece, or detached from the external socket and separated from the main body. The controlling-driving module is disposed within the main body, allows to be electrically connected by the gas guider to control operations of the gas guider in an enabled state and a disabled state, and includes a connection port, which allows the gas detection module to be inserted and driven in an electrical connection, so that the gas detection module detects the gas outside the main body to obtain a gas detection datum, and the gas detection datum is outputted to the controlling-driving module to control the operations of the gas guider in the enabled state and the disabled state.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
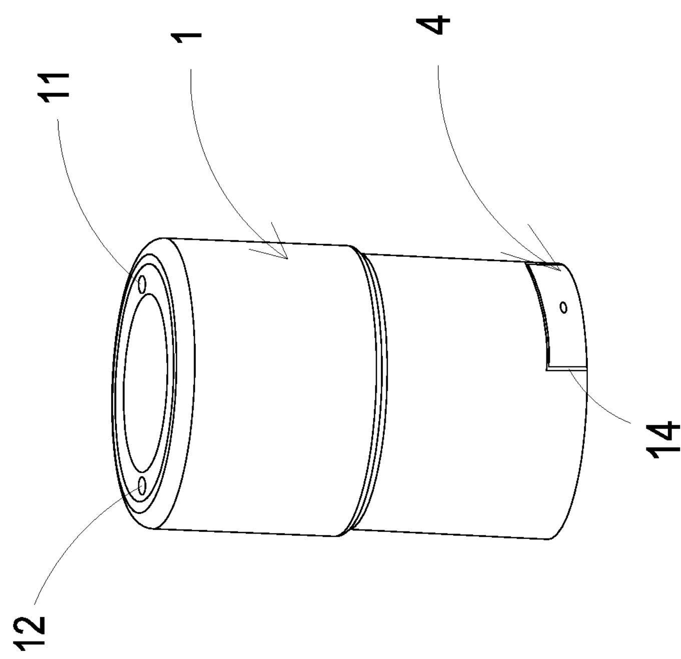
FIG. 1A is a schematic view illustrating a gas detection purification device according to an embodiment of the present disclosure.
Figure 1B:
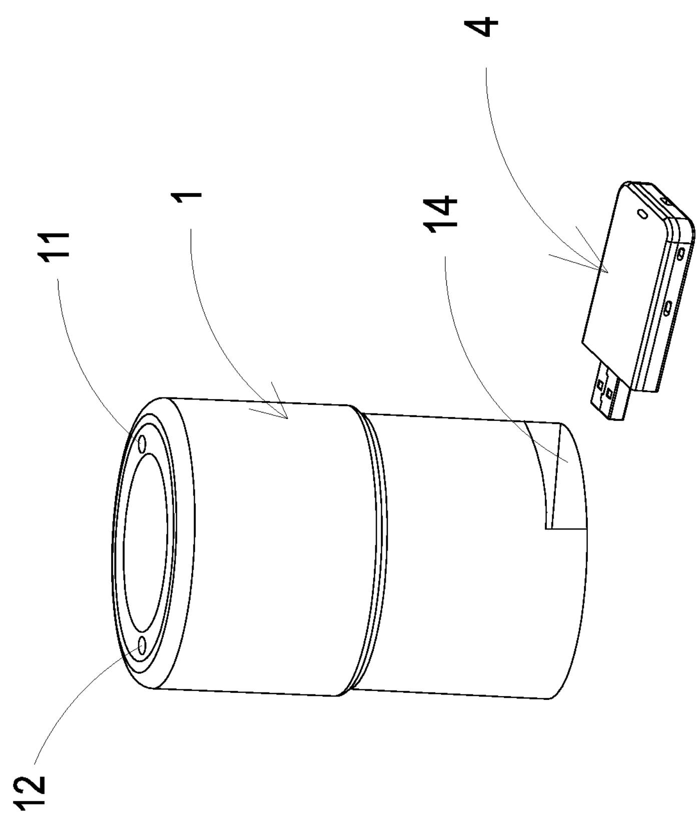
FIG. 1B is a schematic view illustrating the gas detection purification device having the gas detection module detached according to the embodiment of the present disclosure.
Figure 2A:
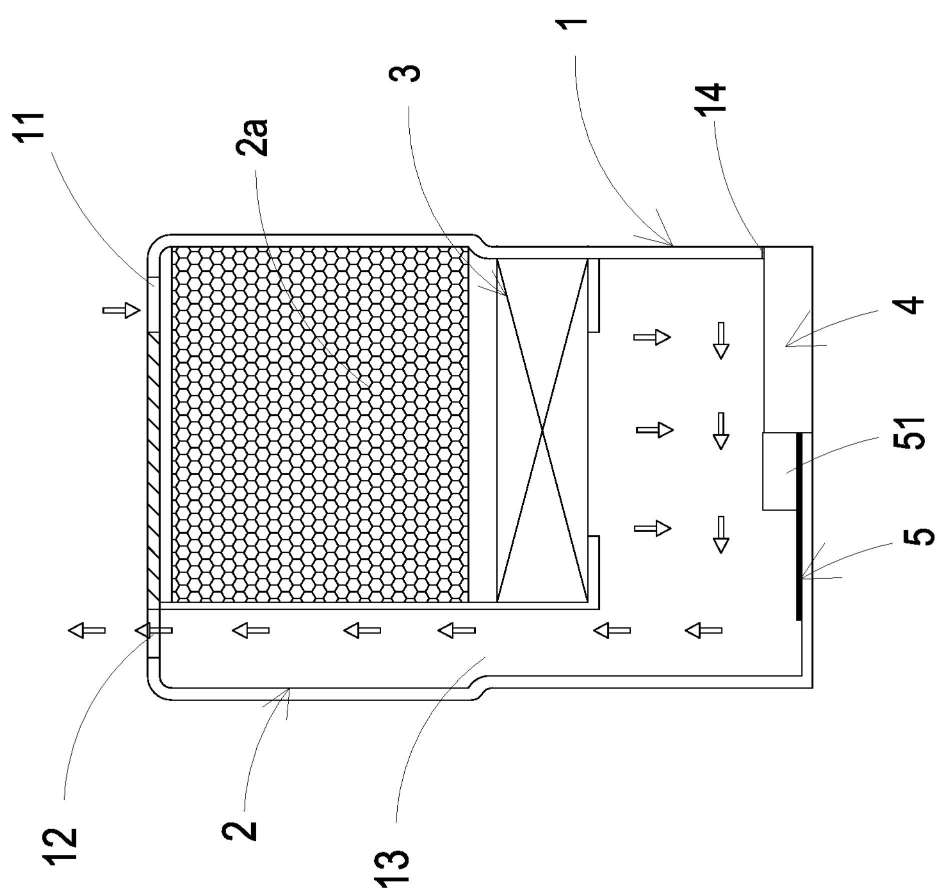
FIG. 2A is a schematic cross-sectional view illustrating a purification unit of the gas detection purification device according to a first embodiment of the present disclosure.

Please refer to FIGS. 1A to 1B and FIG. 2A. The present disclosure provides a gas detection purification device including a main body 1, a purification unit 2, a gas guider 3, a gas detection module 4 and a controlling-driving module 5. The main body 1 includes at least one inlet 11, at least one outlet 12, a gas-flow channel 13 and an external socket 14. The gas-flow channel 13 is disposed between the at least one inlet 11 and the at least one outlet 12. The purification unit 2 is disposed in the gas-flow channel 13 for filtering gas introduced through the gas-flow channel 13. The gas guider 3 is disposed in the gas-flow channel 13 and located at a side of the purification unit 2. The gas is inhaled through the at least one inlet 11, flows through the purification unit 2 for filtration and purification, and is discharged out through the at least one outlet 12. The gas detection module 4 is plugged into the external socket 14 and integrally connected to the main body 1 as one piece, or detached from the external socket 14 and separated from the main body 1. It is conducive to individual maintenance and replacement of the gas detection module 4. The controlling-driving module 5 is disposed within the main body 1, allows to be electrically connected by the gas guider 3 to control operations of the gas guider 3 in an enabled state and a disabled state. The controlling-driving module 5 includes a connection port 51, which allows the gas detection module 4 to be inserted and driven in an electrical connection, so that the gas detection module 4 detects the gas outside the main body 1 to obtain a gas detection datum, and the gas detection datum is outputted to the controlling-driving module 5 to control the operations of the gas guider 3 in the enabled state and the disabled state.

Figure 1C:
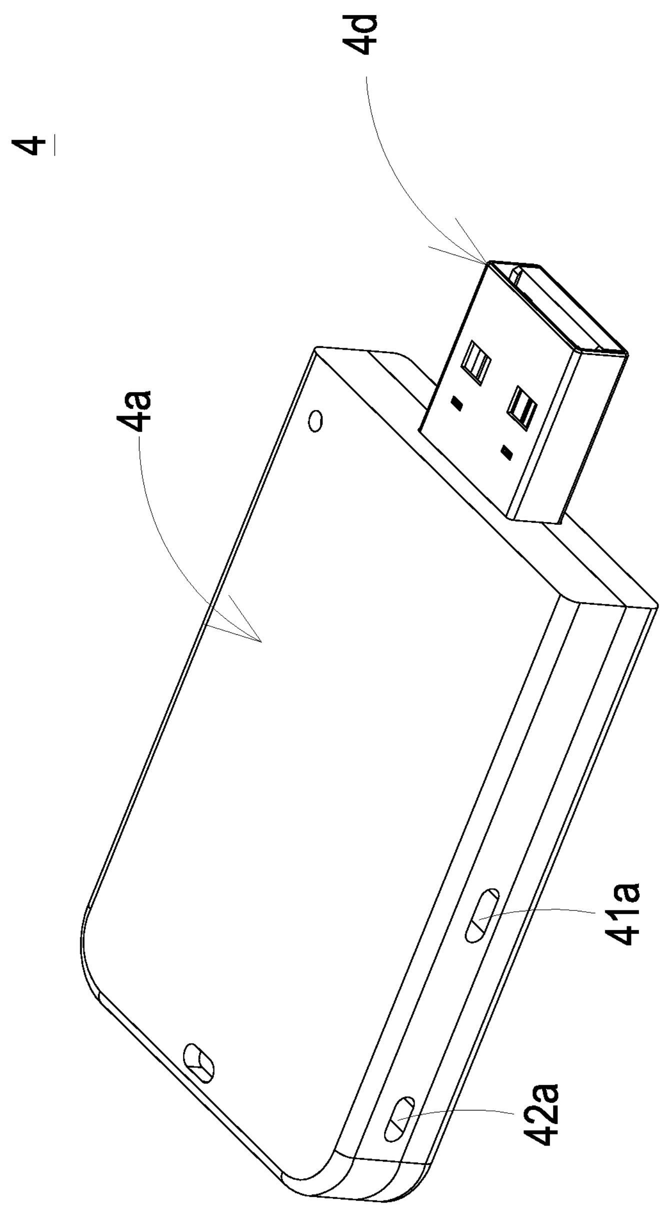
FIG. 1C is a schematic exterior view illustrating the gas detection module of the gas detection purification device according to the embodiment of the present disclosure.
Figure 1D:
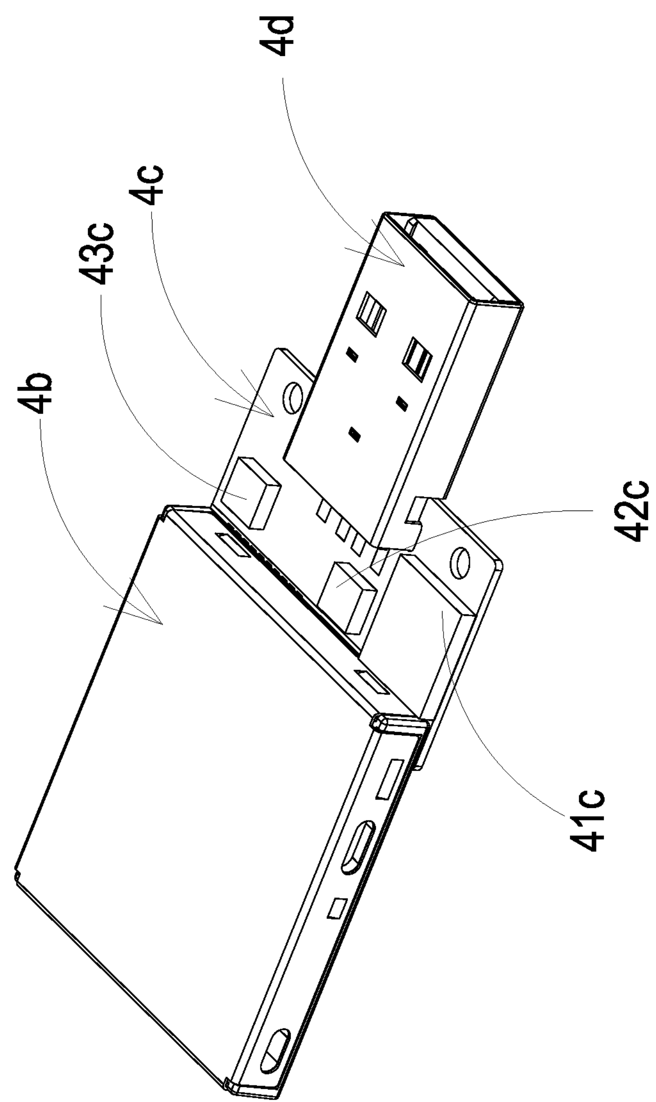
FIG. 1D is a schematic interior view illustrating the related components of the gas detection module of the gas detection purification device according to the embodiment of the present disclosure.
Figure 13:
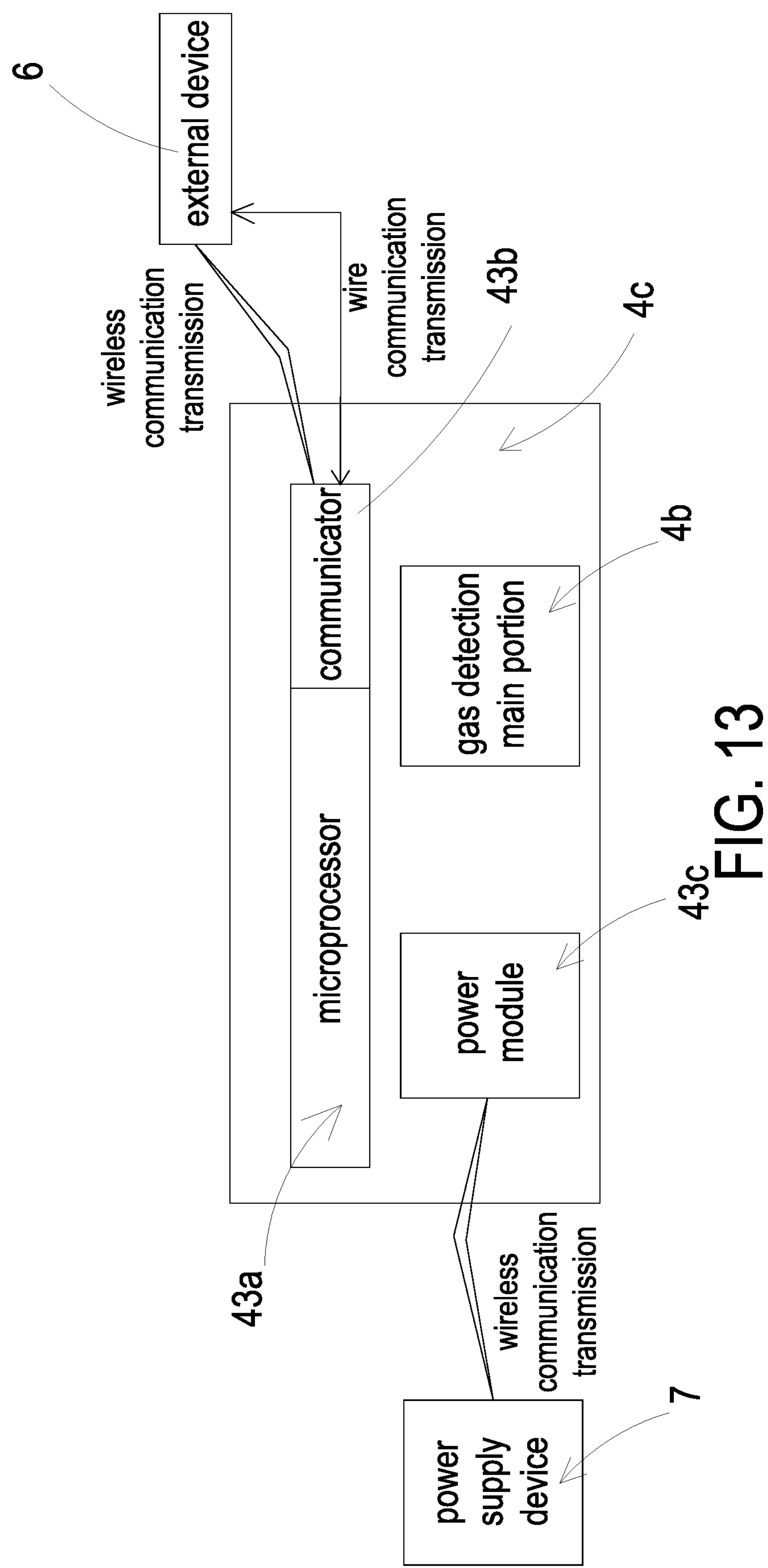
FIG. 13 a block diagram illustrating a configuration of a control circuit unit and the related components of the gas detection purification device according to an embodiment of the present disclosure.

Please refer to FIG. 1C, FIG. 1D and FIG. 13. In the embodiment, the gas detection module 4 includes a housing 4*a*, a gas detection main part 4*b*, a control circuit unit 4*c* and an external connection device 4*d*. In the embodiment, the gas detection main part 4*b*, the control circuit unit 4*c* and the external connection are 4*d* are covered by the housing 4*a* for protection. The external connection device 4*d* is exposed out of the housing 4*a* for correspondingly connecting to the connection port 51 of the controlling-driving module 5, so that the gas detection module 4 is in electrical connection and capable of data transmitting. In the embodiment, the housing 4*a* includes at least one gas inlet 41*a* and at least one gas outlet 42*a*. The gas detection main part 4*b* is disposed within the housing 4*a* and packaged with the control circuit unit 4*c* to form one piece. The gas detection main part 4*b* is in communication with the at least one gas inlet 41*a* and the at least one gas outlet 42*a* of the housing 4*a* for detecting the gas introduced from the outside of the housing 4*a* to obtain the gas detection datum. In the embodiment, the control circuit unit 4*c* includes a microprocessor 41*c*, a communicator 42*c* and a power module 43*c* integrally packaged into one piece in electrical connection. In the embodiment, the power module 43*c* wirelessly transmits, receives and stores electrical energy through a power supply device 7, so as to provide the microprocessor 41*c* for operation. The microprocessor 41*c* receives a gas detection signal of the gas detection main part 4*b*, which is processed and converted into the gas detection datum. The communicator 42*c* is used to receive the gas detection datum outputted from the microprocessor 41*c* and externally transmit the gas detection datum to an external device 6 through a communication transmission for storing. Thereby, the external device 6 generates gas detection information and an alarm notice. In the embodiment, the external connection device 4*d* is disposed on the control circuit unit 4*c* and packaged into one piece in electrical connection. In that, the gas detection module 4 is plugged into the external socket 14 through the external connection device 4*d* and integrally connected to the main body 1 as one piece. Thus, the gas detection main part 4*d* detects the gas outside the main body 1 to generate a gas detection signal, which is received, calculated, processed and converted into the gas detection datum by the microprocessor 41*c*, and the gas detection datum is outputted to the controlling-driving module 5 to control the operations of the gas guider 3 in the enabled state and the disabled state. In contrast, the gas detection module 4 is detached from the external socket 14 through the external connection device **4*d* and separated from the main body 1. It is conducive to individual maintenance and replacement of the gas detection module 4. Preferably but not exclusively, the external device 6** is one selected from the group consisting of a cloud system, a portable device and a computer system. Preferably but not exclusively, the communication transmission is a wire communication transmission or a wireless communication transmission, the wire communication transmission is a USB transmission, and the wireless communication transmission is one selected from the group consisting of Wi-Fi transmission, a radio frequency identification transmission, Bluetooth transmission and a near field communication (NFC) transmission.

Please refer to FIGS. 2A to 2E. The above-mentioned purification unit 2 is disposed in the gas-flow channel 13 and capable of being implemented in various embodiments. Preferably but not exclusively, as shown in FIG. 2A, the purification unit 2 is a filter unit, which includes a filter screen **2*a*. In the embodiment, the gas is introduced into the gas-flow channel 13 by the gas guider 3, and is filtered through the filter screen 2*a* to adsorb the chemical smoke, bacteria, dust particles and pollen contained in the gas. Thus, the effects of filtration and purification are achieved. Preferably but not exclusively, the filter screen 2*a*** is one selected from the group consisting of an electrostatic filter screen, an activated carbon filter screen and a high efficiency particulate air (HEPA) filter screen.

Figure 2B:
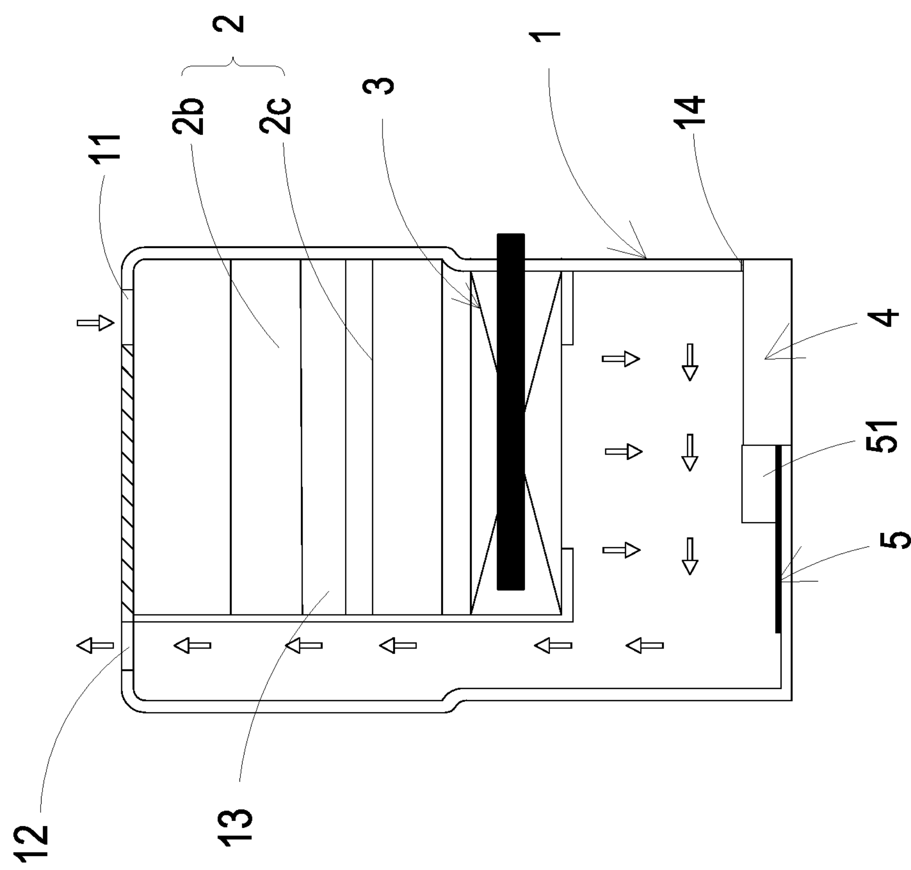
FIG. 2B is a schematic cross-sectional view illustrating a purification unit of the gas detection purification device according to a second embodiment of the present disclosure.

Preferably but not exclusively, as shown in FIG. 2B, the purification unit 2 is a photo-catalyst unit, which includes a photo-catalyst **2*b* and an ultraviolet lamp 2*c* disposed in the gas-flow channel 13, respectively, and spaced apart from each other at a distance. In the embodiment, the gas is introduced into the gas-flow channel 13 by the gas guider 3, and the photo-catalyst 2*b* is irradiated with the ultraviolet lamp 2*c* to convert light energy into chemical energy, which makes a chemical reaction to dispose harmful gases and disinfect bacteria contained in the gas, so that the gas introduced is purified, and the effects of filtration and purification are achieved. In an embodiment, the purification unit 2 is a photo-catalyst unit combined with the filter screen 2*a* as shown in FIG. 2A, which are disposed in the gas-flow channel 13 together to enhance the effects of filtration and purification. Preferably but not exclusively, the filter screen 2*a*** is one selected from the group consisting of an electrostatic filter screen, an activated carbon filter screen and a high efficiency particulate air (HEPA) filter screen.

Figure 2C:
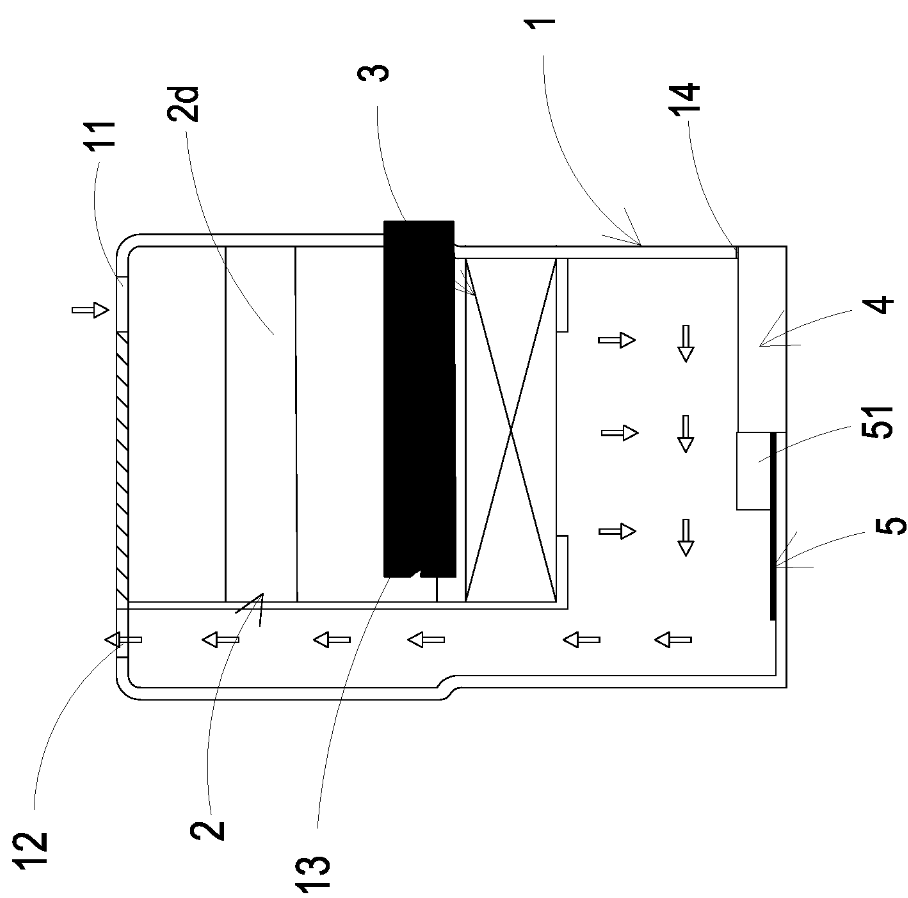
FIG. 2C is a schematic cross-sectional view illustrating a purification unit of the gas detection purification device according to a third embodiment of the present disclosure.

Preferably but not exclusively, as shown in FIG. 2C, the purification unit 2 is a photo-plasma unit, which includes a nanometer irradiation tube **2*d* disposed within the gas-flow channel 13. When the gas is introduced into the gas-flow channel 13 by the gas guider 3, the gas is irradiated by the nanometer irradiation tube 2*d*, whereby the gas is purified. Consequently, oxygen molecules and water molecules contained in the gas are decomposed into high oxidizing photo-plasma, which is ion flow capable of destroying organic molecules. In that, volatile formaldehyde, volatile toluene and volatile organic (VOC) gases contained in the gas are decomposed into water and carbon dioxide, so as to achieve the effects of filtration and purification. In an embodiment, the purification unit 2 is a photo-plasma unit combined with the filter screen 2*a* as shown in FIG. 2A, which are disposed in the gas-flow channel 13 together to enhance the effects of filtration and purification. Preferably but not exclusively, the filter screen 2*a*** is one selected from the group consisting of an electrostatic filter screen, an activated carbon filter screen and a high efficiency particulate air (HEPA) filter screen.

Figure 2D:
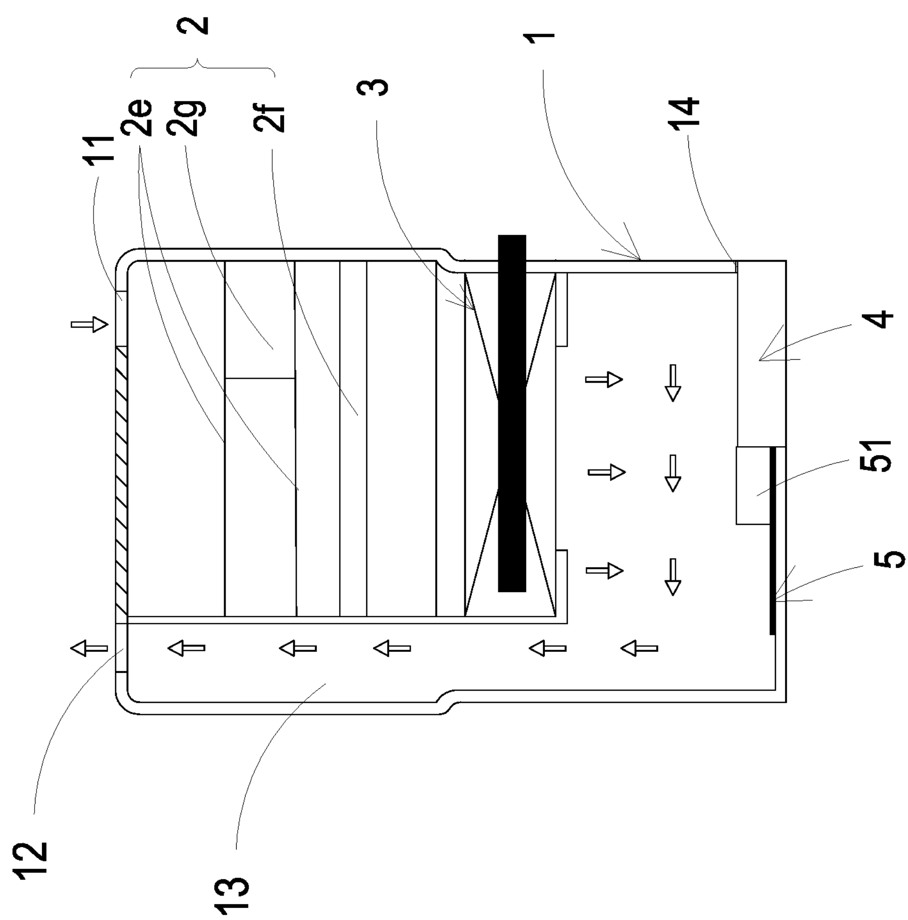
FIG. 2D is a schematic cross-sectional view illustrating a purification unit of the gas detection purification device according to a fourth embodiment of the present disclosure.

Preferably but not exclusively, as shown in FIG. 2D, the purification unit 2 is a negative ionizer, which includes at least one electrode wire **2*e*, at least one dust collecting plate 2*f* and a boost power supply device 2*g*. Each electrode wire 2*e* and each dust collecting plate 2*f* are disposed within the gas-flow channel 13. When a high voltage is provided from the boost power supply device 2*g* to the at least one electrode wire 2*e* to discharge, the dust collecting plate 2*f* has negative charge. When the gas is introduced into the gas-flow channel 13 by the gas guider 3, each electrode wire 2*e* discharges to make fine particles in the gas to have positive charge, and fine particles having positive charge are attached to the dust collecting plate 2*f* negatively charged, so as to achieve the effects of filtration and purification. In an embodiment, the purification unit 2 is a negative ionizer combined with the filter screen 2*a* as shown in FIG. 2A, which are disposed in the gas-flow channel 13 together, to enhance the effects of filtration and purification. Preferably but not exclusively, the filter screen 2*a*** is one selected from the group consisting of an electrostatic filter screen, an activated carbon filter screen and a high efficiency particulate air (HEPA) filter screen.

Figure 2E:
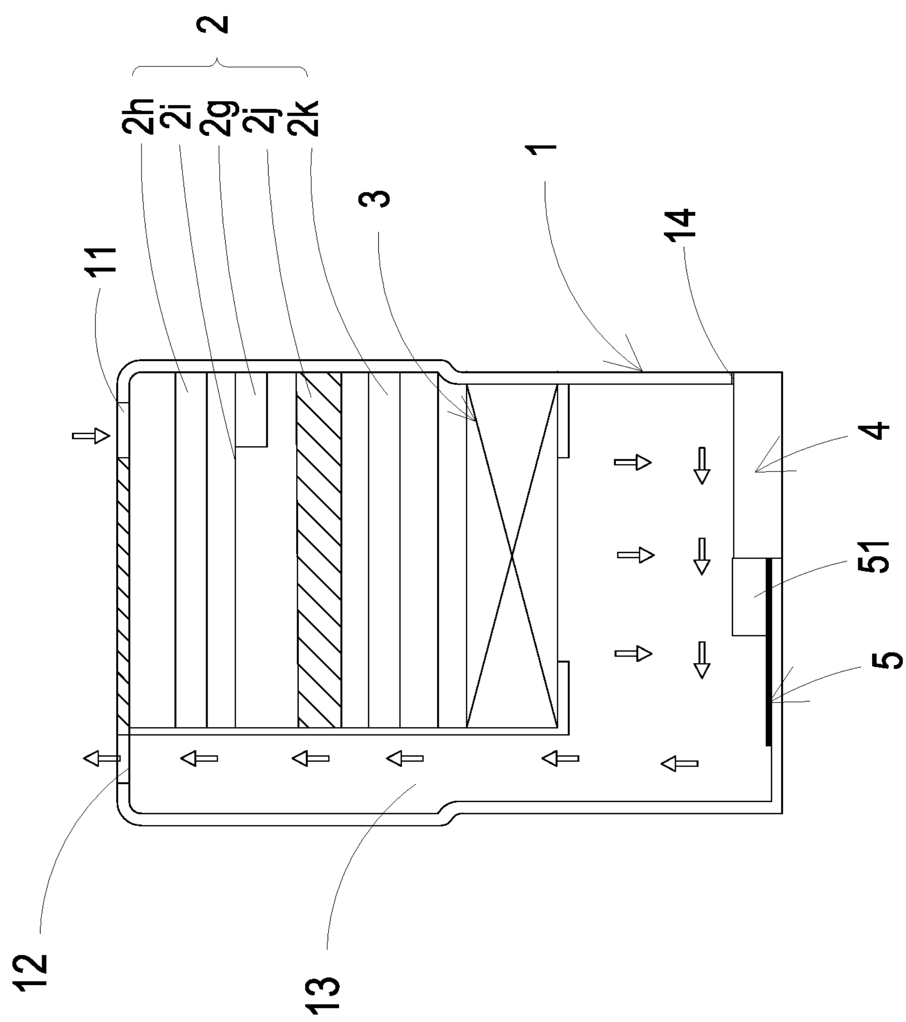
FIG. 2E is a schematic cross-sectional view illustrating a purification unit of the gas detection purification device according to a fifth embodiment of the present disclosure.

Preferably but not exclusively, as shown in FIG. 2E, the purification unit 2 is a plasma ion unit, which includes an upper electric-field protection screen **2*h*, a high efficiency particulate air filter screen 2*i*, a high-voltage discharge electrode 2*j*, a lower electric-field protection screen 2*k* and a boost power supply device 2*g*. The upper electric-field protection screen 2*h*, the high efficiency particulate air filter screen 2*i*, the high-voltage discharge electrode 2*j* and the lower electric-field protection screen 2*k* are disposed within the gas-flow channel 13. The high efficiency particulate air filter screen 2*i* and the high-voltage discharge electrode 2*j* are located between the upper electric-field protection screen 2*h* and the lower electric-field protection screen 2*k*. When a high voltage is provided from the boost power supply device 2*g* to the high-voltage discharge electrode 2*j* to discharge, a high-voltage plasma column with plasma ion is formed. When the gas is introduced into the gas-guiding channel 13 by the gas guider 3, oxygen molecules and water molecules contained in the gas are decomposed into positive hydrogen ions ($H^+$) and negative oxygen ions (02) through the plasma ion. The positive hydrogen ($H^+$) and negative oxygen (02) ions surrounding substances attached with water are bonded on the surface of viruses and bacteria and changed into OH radicals. With their extremely strong oxidizing power, the OH radicals rapidly extract hydrogen (H) from the protein on the surface of viruses and bacteria, thus decomposing the protein and suppressing activity. Removing the hydrogen atom (H) from this structure inactivates the undesirable substance, so as to achieve the effects of filtration and purification. In an embodiment, the purification unit 2 is a plasma ion unit combined with the filter screen 2*a* as shown in FIG. 2A, which are disposed in the gas-flowing channel 13 together to enhance the effects of filtration and purification. Preferably but not exclusively, the filter screen 2*a*** is one selected from the group consisting of an electrostatic filter screen, an activated carbon filter screen and a high efficiency particulate air (HEPA) filter screen.

Preferably but not exclusively, the gas guider 3 is a fan, such as a vortex fan or a centrifugal fan. Alternatively, the gas guider 3 is an actuating pump 30, as shown in FIGS. 3A, 3B, 4A and 4B. In the embodiment, the actuating pump 30 includes a gas inlet plate 301, a resonance plate 302, a piezoelectric actuator 303, a first insulation plate 304, a conducting plate 305 and a second insulation plate 306, which are stacked on each other sequentially. In the embodiment, the gas inlet plate 301 includes at least one inlet aperture 301*a*, at least one convergence channel 301*b* and a convergence chamber 301*c*. The at least one gas inlet aperture 301*a* is disposed to inhale the gas. The at least one gas inlet aperture 301*a* correspondingly penetrates through the at least one convergence channel 301*b*, and the at least one convergence channel 301*b* is converged into the convergence chamber 301*c*. In that, the gas inhaled through the at least one gas inlet aperture 301*a* is converged into the convergence chamber 301*c*. The number of the gas inlet apertures 301*a* is the same as the number of the convergence channels 301*b*. In the embodiment, the number of the gas inlet apertures 301*a* and the convergence channels 301*b* is exemplified by four for each but not limited thereto. The four gas inlet apertures 301*a* penetrate through the four convergence channels 301*b* respectively, and the four convergence channels 301*b* converge to the convergence chamber 301*c*.

Figure 3A:
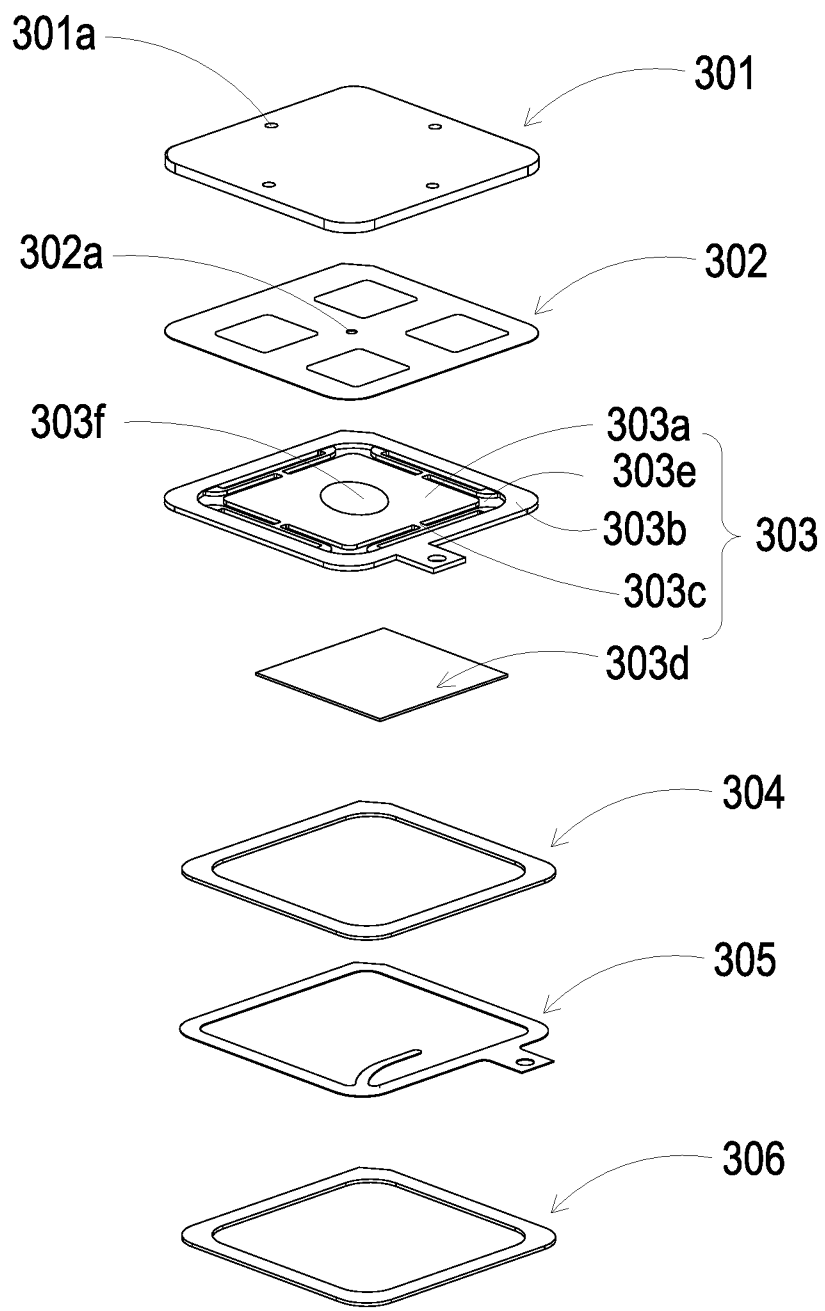
FIG. 3A is a schematic exploded view illustrating the related components of the actuating pump of the gas detection purification device according to the embodiment of the present disclosure and taken from a front perspective.
Figure 3B:
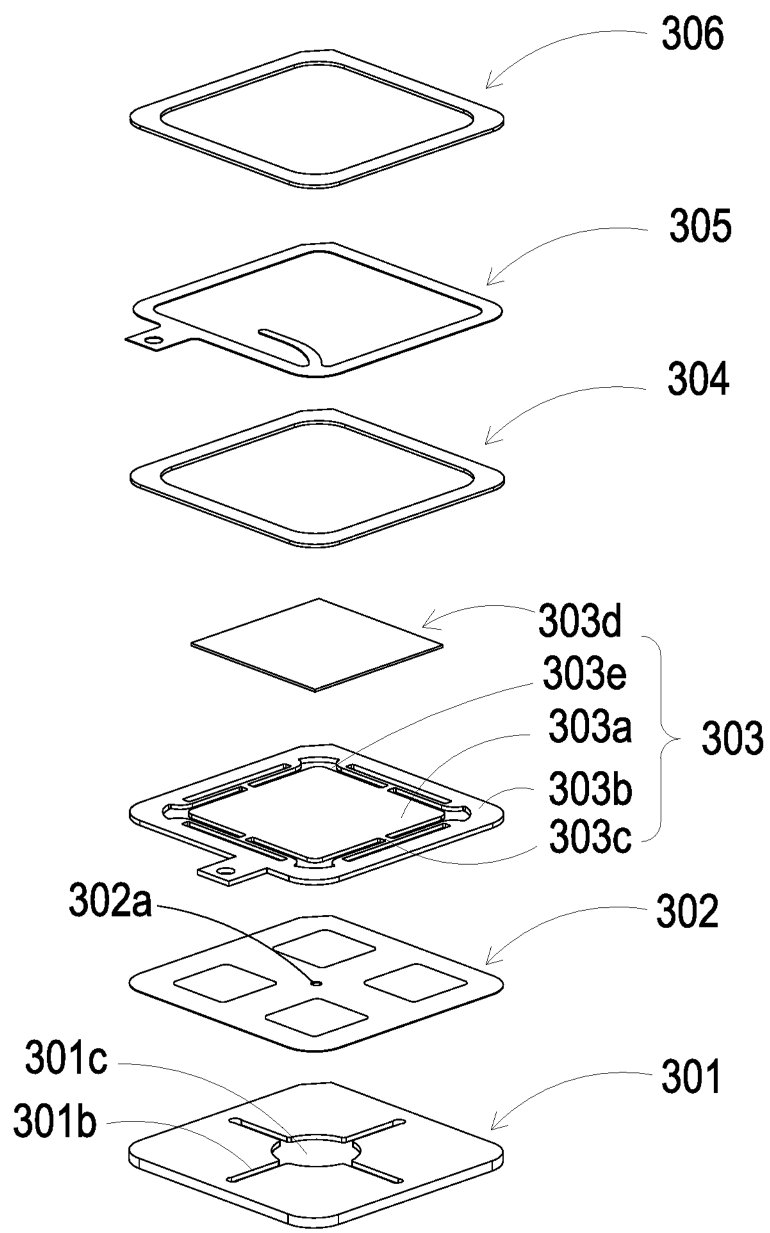
FIG. 3B is a schematic exploded view illustrating the related components of the actuating pump of the gas detection purification device according to the embodiment of the present disclosure and taken from a rear perspective.
Figure 4A:
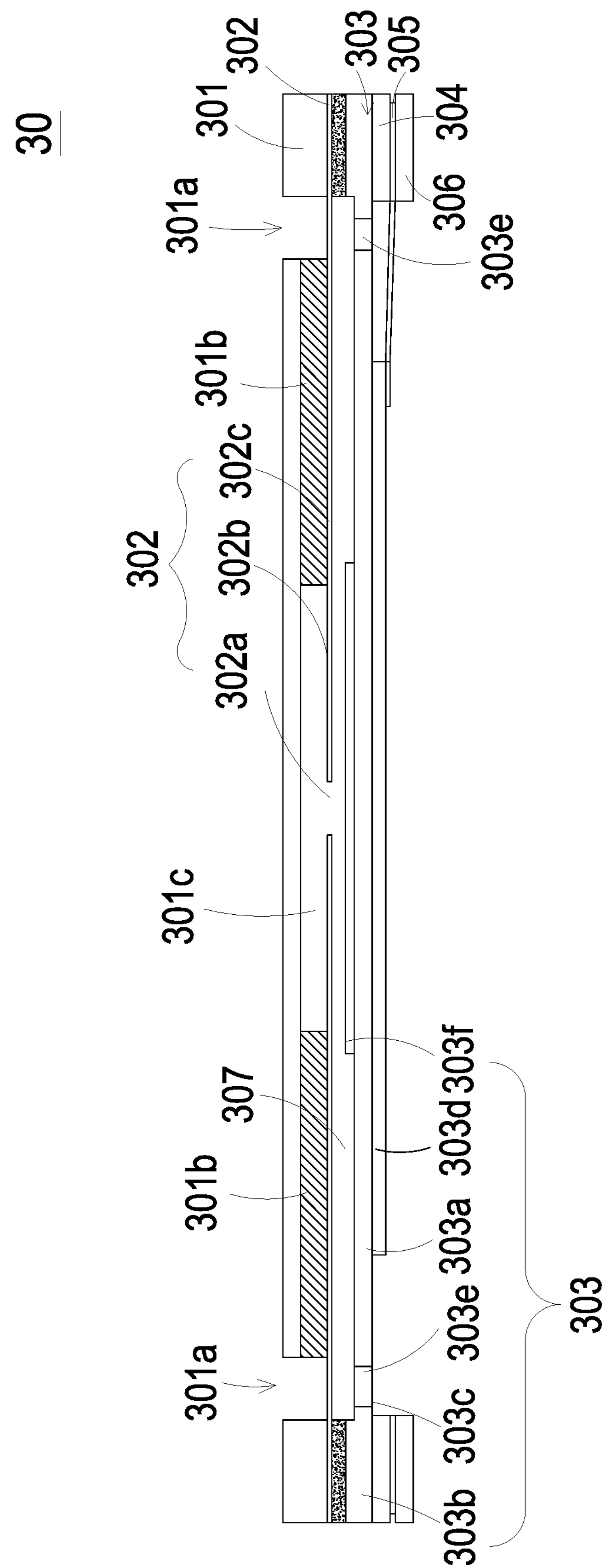
FIG. 4A is a schematic cross-sectional view illustrating the actuating pump of the gas detection purification device according to an embodiment of the present disclosure.

Please refer to FIGS. 3A, 3B and 4A. The resonance plate 302 is assembled on the gas inlet plate 301 by attaching. The resonance plate 302 has a central aperture 302*a*, a movable part 302*b* and a fixed part 302*c*. The central aperture 302*a* is located at a center of the resonance plate 302 and corresponds in position to the convergence chamber 301*c* of the gas inlet plate 301. The movable part 302*b* surrounds the central aperture 302*a* and corresponds in position to the convergence chamber 301*c*. The fixed part 302*c* is disposed around the periphery of the resonance plate 302 and securely attached on the gas inlet plate 301.

Please refer to FIGS. 3A, 3B and 4A, again. The piezoelectric actuator 303 includes a suspension plate 303*a*, an outer frame 303*b*, at least one bracket 303*c*, a piezoelectric element 303*d*, at least one vacant space 303*e* and a bulge 303E The suspension plate 303*a* is square-shaped because the square suspension plate 303*a* is more power-saving than the circular suspension plate. Generally, the consumed power of the capacitive load at the resonance frequency is positively related to the resonance frequency. Since the resonance frequency of the square suspension plate 303*a* is obviously lower than that of the circular square suspension plate, the consumed power of the square suspension plate 303*a* is fewer. Therefore, the square suspension plate 303*a* in this embodiment has the effectiveness of power-saving. In the embodiment, the outer frame 303*b* is disposed around the periphery of the suspension plate 303*a*. The at least one bracket 303*c* is connected between the suspension plate 303*a* and the outer frame 303*b* for elastically supporting the suspension plate 303*a*. The piezoelectric element 303*d* has a side, and a length of the side of the piezoelectric element 303*d* is less than or equal to that of the suspension plate 303*a*. The piezoelectric element 303*d* is attached on a surface of the suspension plate 303*a*. When a voltage is applied to the piezoelectric element 303*d*, the suspension plate 303*a* is driven to undergo the bending vibration. The at least one vacant space 303*e* is formed among the suspension plate 303*a*, the outer frame 303*b* and the at least one bracket 303*c* for allowing the gas to flow through. The bulge 303*f* is formed on a surface of the suspension plate 303*a*, which is opposite to the surface of the suspension plate 303*a* attached on the piezoelectric element 303*d*. In this embodiment, the formation of the bulge 303*f* may be completed by using an etching process on the suspension plate 303*a*. Accordingly, the bulge 303*f* of the suspension plate 303*a* is integrally formed and protrudes from the surface opposite to that attached on the piezoelectric element 303*d*, and a stepped structure is formed.

Please refer to FIGS. 3A, 3B and 4A. In the embodiment, the gas inlet plate 301, the resonance plate 302, the piezoelectric actuator 303, the first insulation plate 304, the conducting plate 305 and the second insulation plate 306 are stacked and assembled sequentially. A chamber space 307 is formed between the suspension plate 303*a* and the resonance plate 302, and the chamber space 307 can be formed by filling a gap between the resonance plate 302 and the outer frame 303*b* of the piezoelectric actuator 303 with a material, such as a conductive adhesive, but not limited thereto. Thus, a specific depth between the resonance plate 302 and the suspension plate 303*a* is maintained to allow the gas to pass rapidly. In addition, since the resonance plate 302 and the suspension plate 303*a* are maintained at a suitable distance, so that the contact interference therebetween is reduced and the generated noise is largely reduced. In some other embodiments, the thickness of the conductive adhesive filled into the gap between the resonance plate 302 and the outer frame 303*b* of the piezoelectric actuator 303 is reduced by increasing the height of the outer frame 303*b* of the piezoelectric actuator 303. In that, the suspension plate 303*a* and the resonance plate 302 are maintained at a suitable distance and the thickness of conductive adhesive filled in each of the entire actuating pump 30 is not influenced due to the hot pressing temperature and the cooling temperature. It avoids that the actual size of the chamber space 307 is influenced due to the thermal expansion and contraction after each of the entire actuating pump 30 is assembled. The present disclosure is not limited thereto. In addition, since the transportation effect of the actuating pump 30 is affected by the chamber space 307, it is very important to maintain the chamber space 307 fixed, to provide a stable transportation efficiency of the actuating pump 30.

Figure 4B:
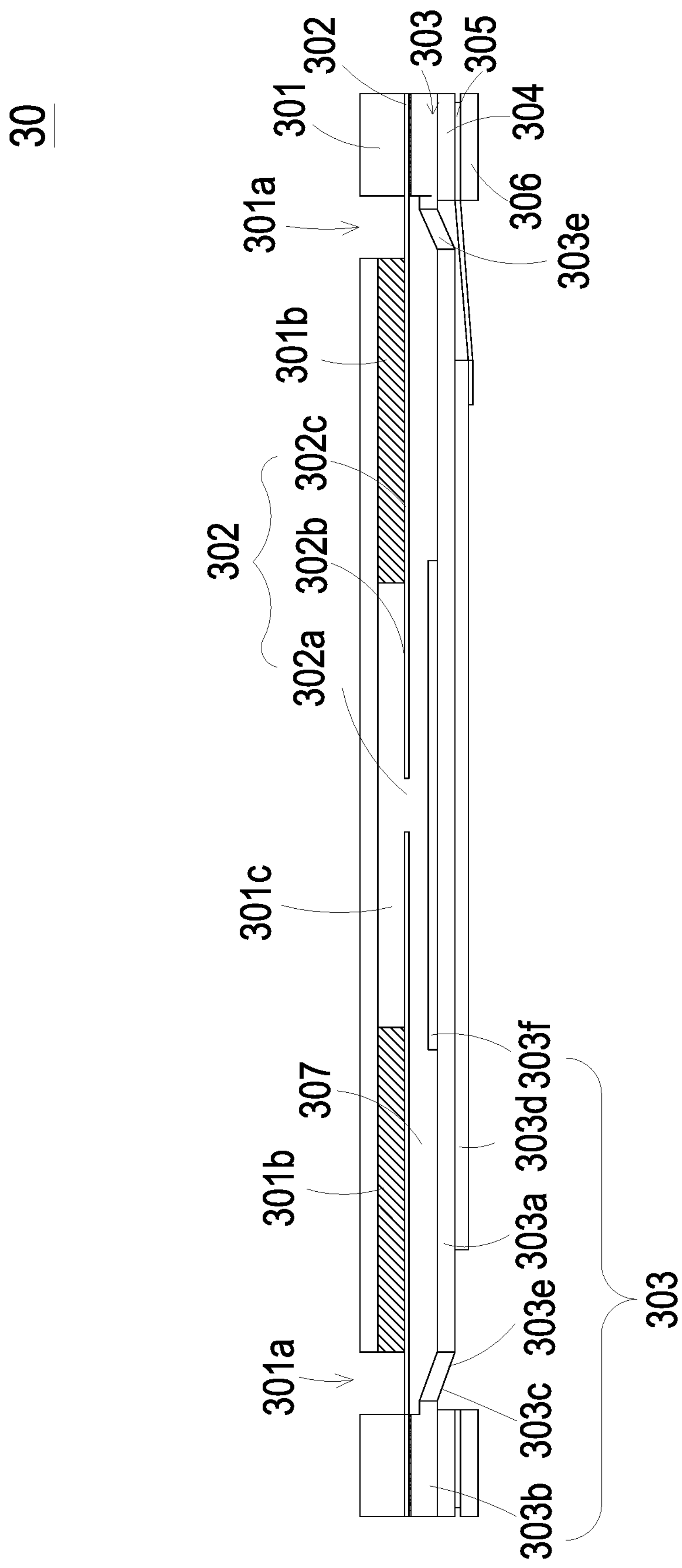
FIG. 4B is a schematic cross-sectional view illustrating the actuating pump of the gas detection purification device according to another embodiment of the present disclosure.

Please refer to FIG. 4B, in some other embodiments of the piezoelectric actuator 303, the suspension plate 303*a* is formed by stamping to make it extend at a distance in a direction away from the resonance plates 302. The extended distance can be adjusted through the at least one bracket 303*c* formed between the suspension plate 303*a* and the outer frame 303*b*. Consequently, the surface of the bulge 303*f* disposed on the suspension plate 303*a* and the surface of the outer frame 303*b* are non-coplanar. By utilizing a small amount of filling materials, such as a conductive adhesive applied to the coupling surface of the outer frame 303*b*, the piezoelectric actuator 303 is attached to the fixed part 302*c* of the resonance plate 302 by hot pressing, thereby assembling the piezoelectric actuator 303 and the resonance plates 302 in combination. Thus, the structure of the chamber space 307 is improved by directly stamping the suspension plate 303*a* of the piezoelectric actuator 303 described above. In this way, the required chamber space 307 can be achieved by adjusting the stamping distance of the suspension plate 303*a* of the piezoelectric actuator 303. It benefits to simplify the structural design of the chamber space 307, and also achieves the advantages of simplifying the process and shortening the processing time. In addition, the first insulating plate 304, the conducting plate 305 and the second insulating plate 306 are all thin frame-shaped sheets, but are not limited thereto, and are sequentially stacked on the piezoelectric actuator 303 to form the entire structure of actuating pump 30.

Figure 4C:
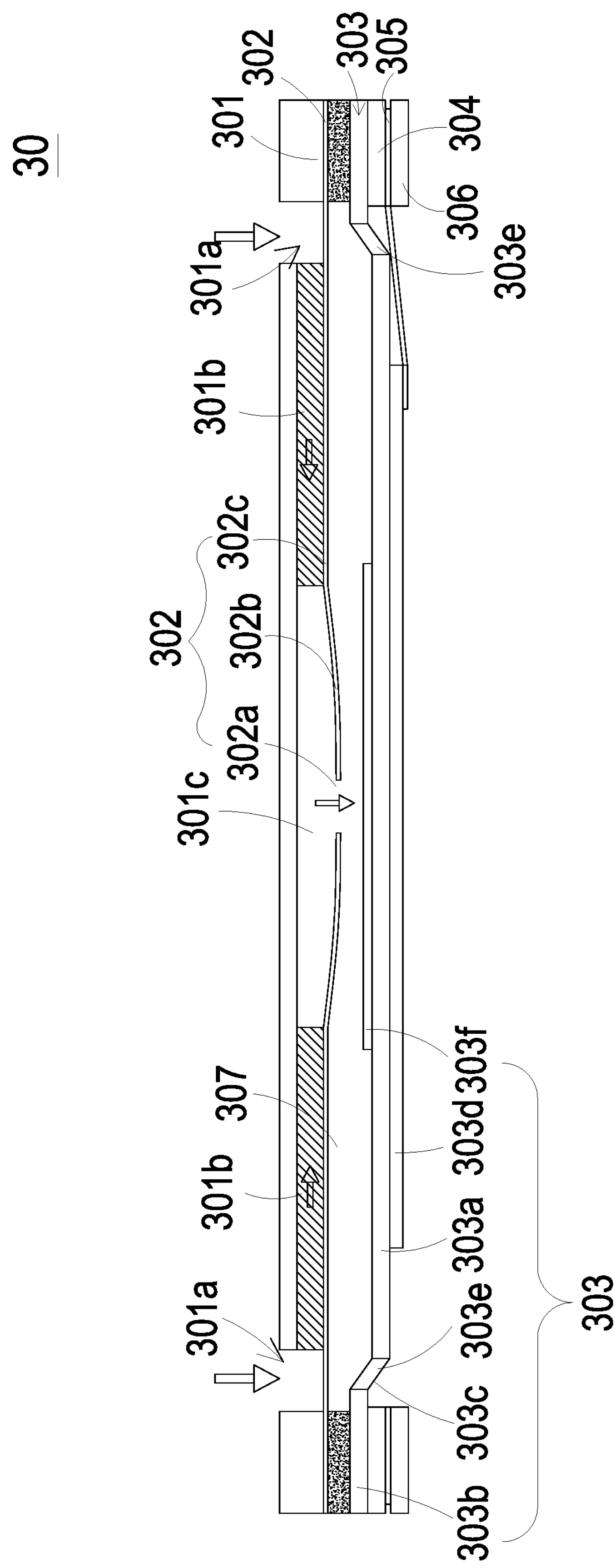
FIGS. 4C to 4E schematically illustrate the actions of the actuating pump of FIG. 4A.
Figure 4D:
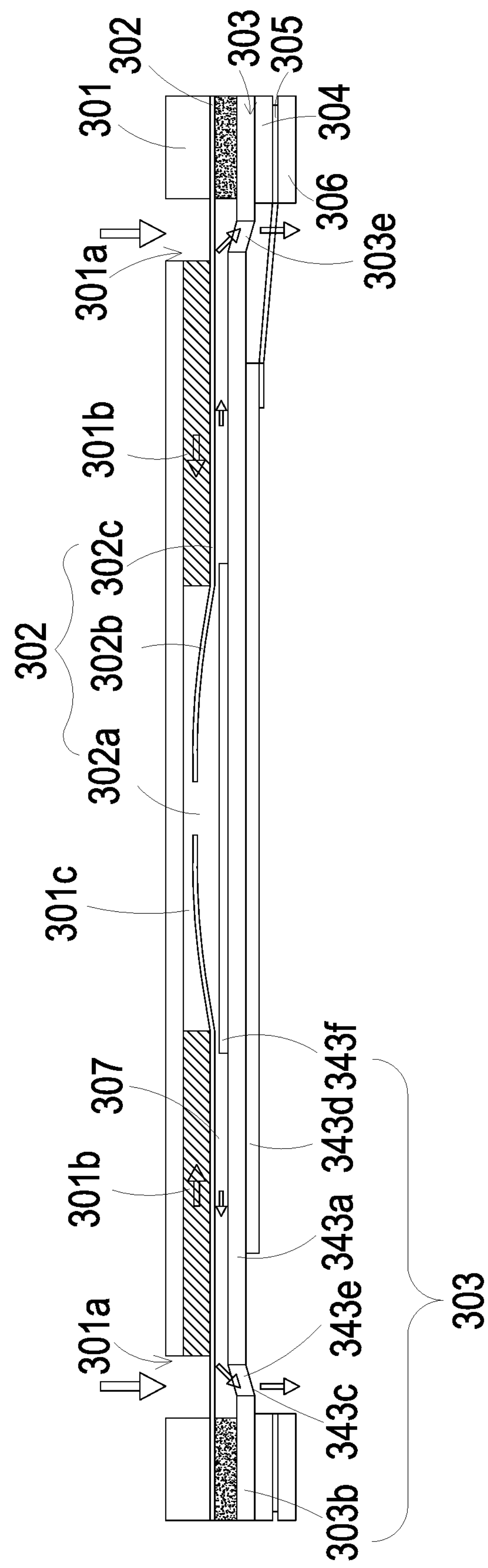
Figure 4E:
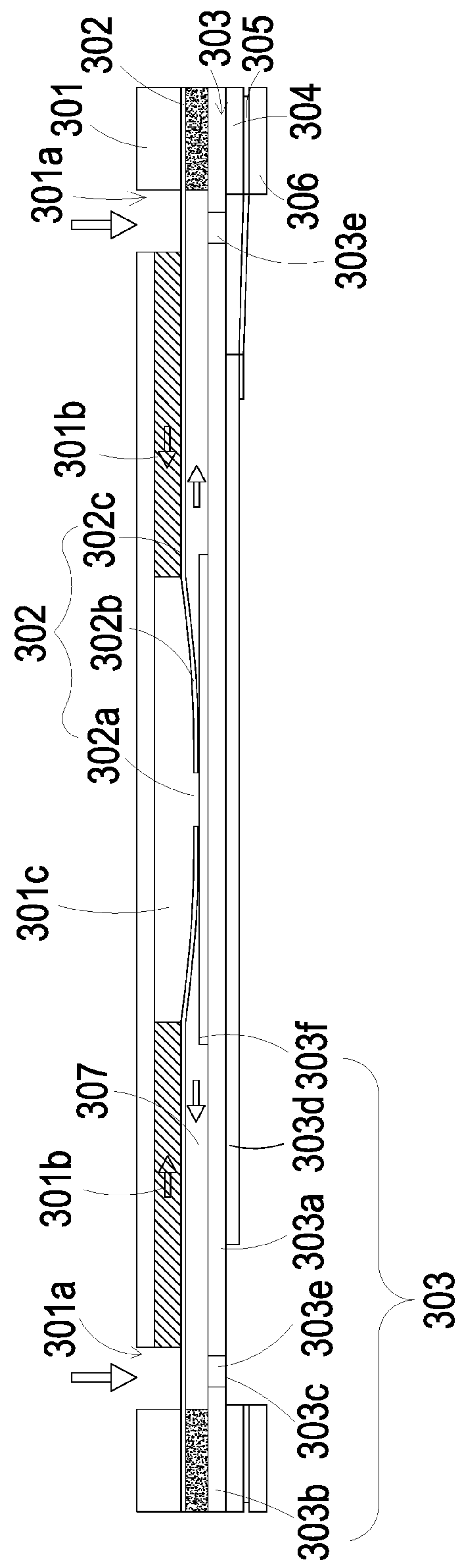

In order to understand the actuations of the actuating pump 30, please refer to FIGS. 4C to 4E. Please refer to FIG. 4C, when the piezoelectric element 303*d* of the piezoelectric actuator 303 is deformed in response to an applied voltage, the suspension plate 303*a* is driven to displace in the direction away from the resonance plate 302. In that, the volume of the chamber space 307 is increased, a negative pressure is formed in the chamber space 307, and the gas in the convergence chamber 301*c* is introduced into the chamber space 307. At the same time, the resonance plate 302 is in resonance and is thus displaced synchronously. Thereby, the volume of the convergence chamber 301*c* is increased. Since the gas in the convergence chamber 301*c* is introduced into the chamber space 307, the convergence chamber 301*c* is also in a negative pressure state, and the gas is sucked into the convergence chamber 301*c* through the gas inlet apertures 301*a* and the convergence channels 301*b*. Then, as shown in FIG. 4D, the piezoelectric element 303*d* drives the suspension plate 303*a* to displace toward the resonance plate 302 to compress the chamber space 307. Similarly, the resonance plate 302 is actuated in resonance to the suspension plate 303*a* and is displaced. Thus, the gas in the chamber space 307 is further transmitted to pass through the vacant spaces 303*e* and it achieves the effectiveness of gas transportation. Finally, as shown in FIG. 4E, when the suspension plate 303*a* is driven to return to an initial state, the resonance plate 302 is also driven to displace. In that, the resonance plate 302 pushes the gas in the chamber space 307 toward the vacant spaces 303*e*, and the volume of the convergence chamber 301*c* is increased. Thus, the gas can continuously pass through the gas inlet apertures 301*a* and the convergence channels 301*b*, and can be converged in the convergence chamber 301*c*. By repeating the actuations illustrated in FIGS. 4C to 4E continuously, the actuating pump 30 can continuously transport the gas at high speed. The gas enters the gas inlet apertures 301*a*, flows through a flow path formed by the gas inlet plate 301 and the resonance plate 3022 with a pressure gradient, and then is transported upwardly through the vacant spaces 303*e*. It achieves the gas transporting operation of the actuating pump 30.

Figure 5A:
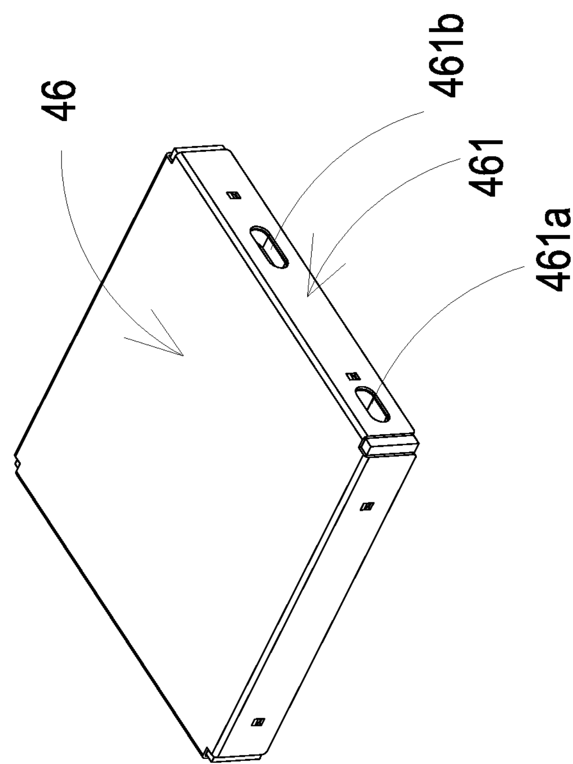
FIG. 5A is schematic exterior view illustrating a gas detection main part according to an embodiment of the present disclosure.
Figure 5B:
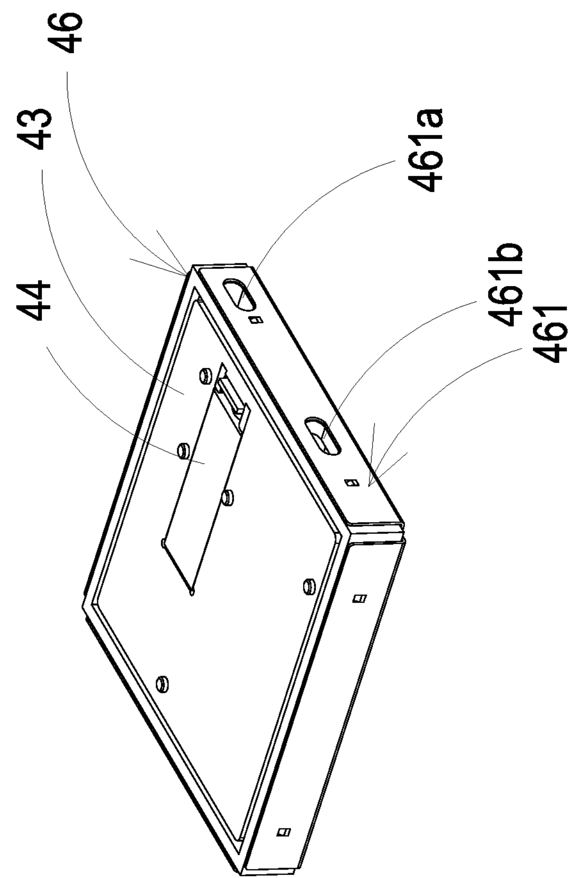
FIG. 5B is a schematic exterior view illustrating the gas detection main part according to the embodiment of the present disclosure and taken from another perspective angle.
Figure 6A:
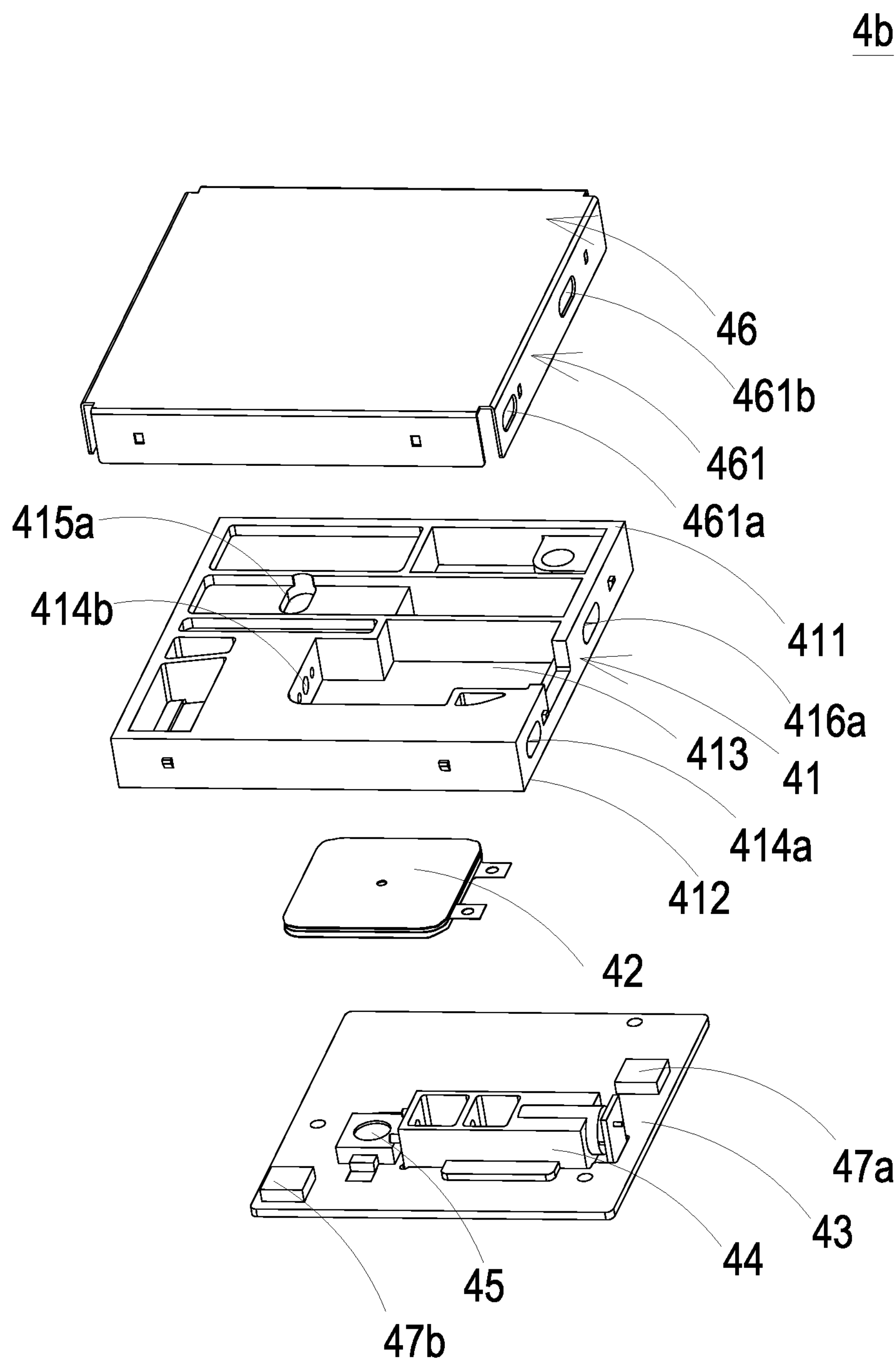
FIG. 6A is a schematic exploded view illustrating the gas detection main part of the present disclosure.
Figure 6B:
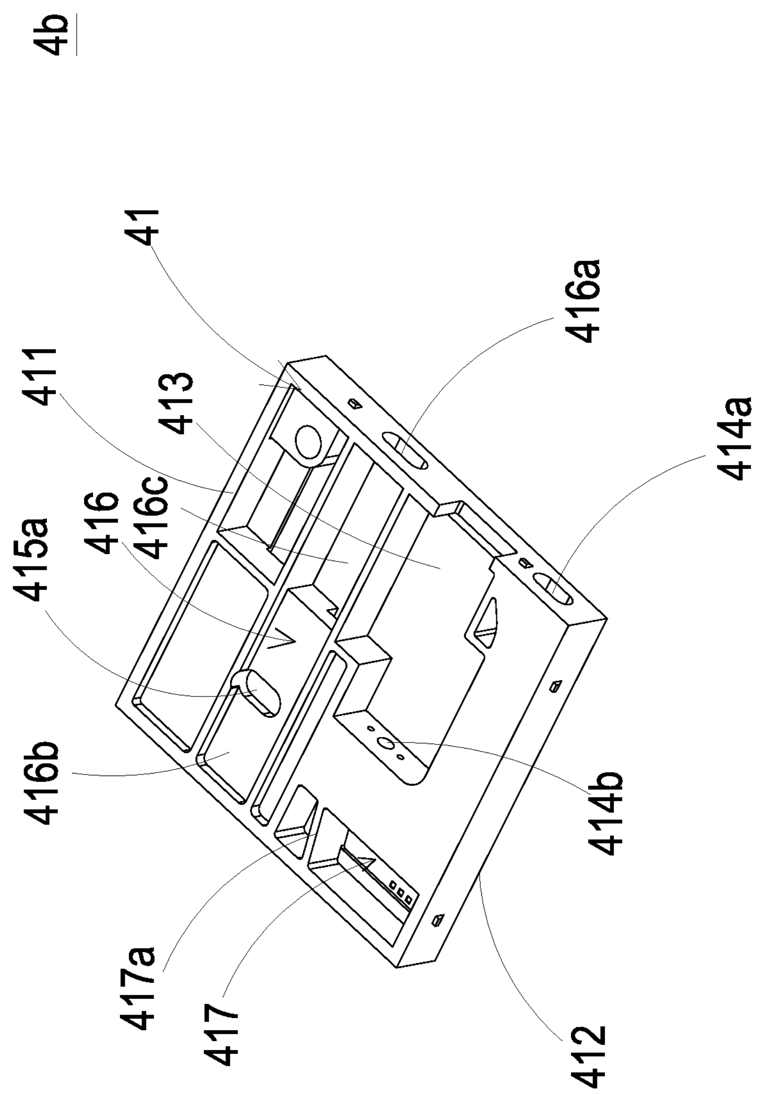
FIG. 6B is a schematic perspective view illustrating a base of the gas detection main part of the present disclosure.
Figure 6C:
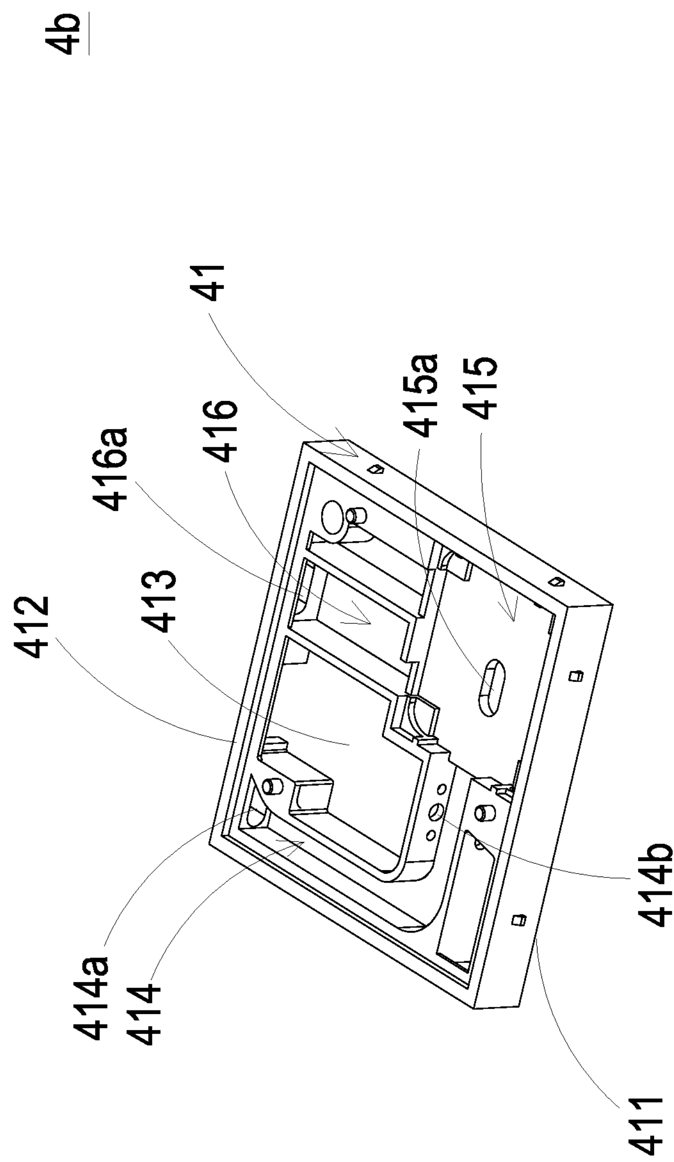
FIG. 6C is a schematic perspective view illustrating the base of the gas detection main part of the present disclosure and taken from another perspective angle.
Figure 7:
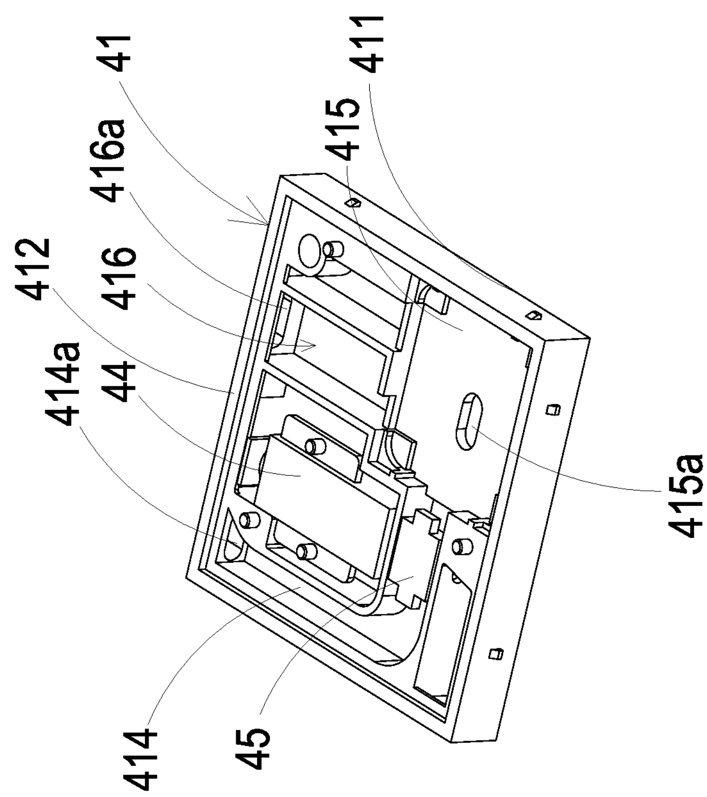
FIG. 7 is a schematic perspective view illustrating a laser component and a particulate sensor accommodated in the base of the present disclosure.
Figure 11A:
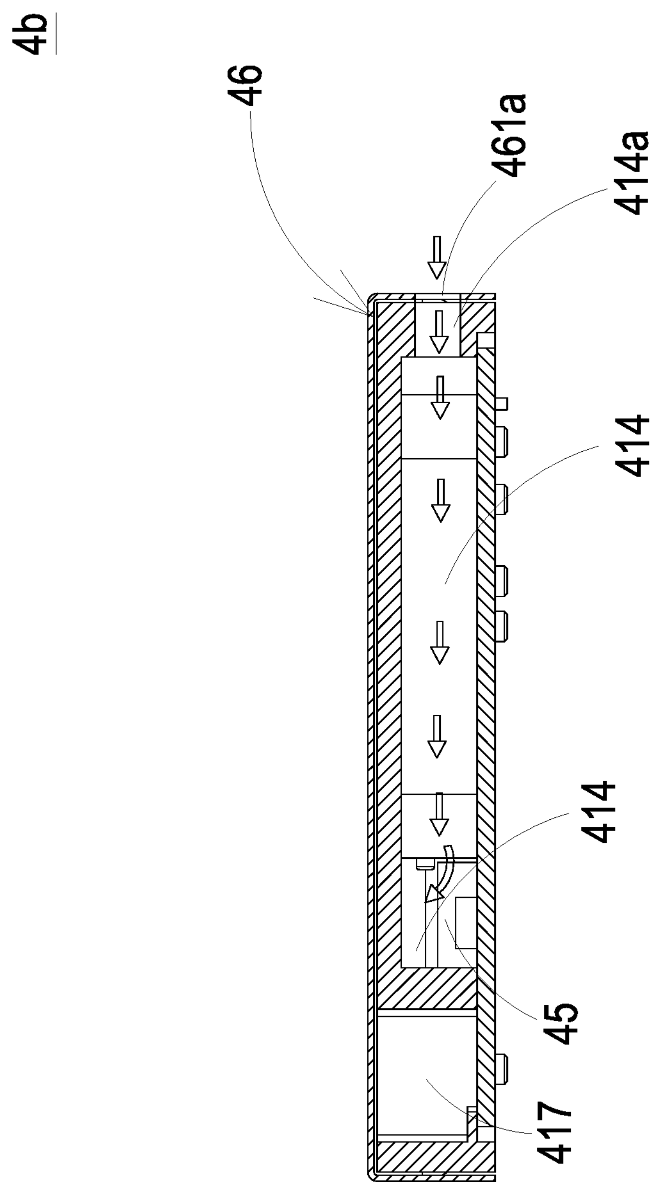
FIGS. 11A to 11C schematically illustrate gas flowing paths of the gas detection main part of the present disclosure.

Please refer to FIGS. 5A to 5B, FIGS. 6A to 6C, FIG. 7 and FIGS. 8A to 8B. In the embodiment, the gas detection main part 4*b* includes a base 41, a piezoelectric actuator 42, a driving circuit board 43, a laser component 44, a particulate sensor 45 and an outer cover 46. The base 41 includes a first surface 411, a second surface 412, a laser loading region 413, a gas-inlet groove 414, a gas-guiding-component loading region 415 and a gas-outlet groove 416. In the embodiment, the first surface 411 and the second surface 412 are two surfaces opposite to each other. In the embodiment, the laser loading region 413 is hollowed out from the first surface 411 to the second surface 412. The gas-inlet groove 414 is concavely formed from the second surface 412 and disposed adjacent to the laser loading region 413. The gas-inlet groove 414 includes a gas-inlet 414*a* and two lateral walls. The gas-inlet 414*a* is in communication with an environment outside the base 41, and spatially corresponds to an inlet opening 461*a* of the outer cover 46. A transparent window 414*b* is opened on the two lateral walls and is in communication with the laser loading region 413. Therefore, the first surface 411 of the base 41 is covered and attached by the outer cover 46, and the second surface 412 is covered and attached by the driving circuit board 43. Thus, the gas-inlet groove 414 defines an inlet path, as shown in FIG. 7 and FIG. 11A.

Figure 11B:
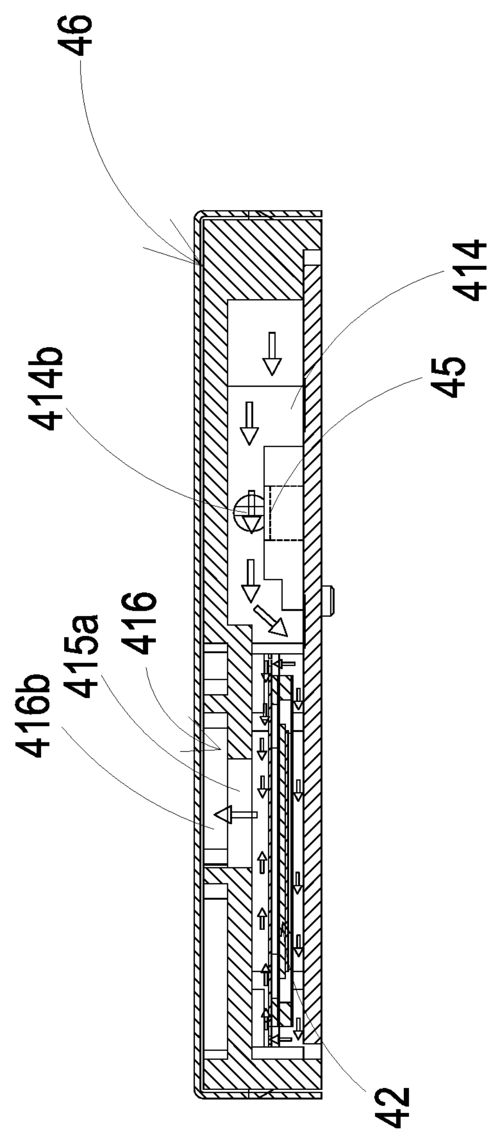
Figure 11C:
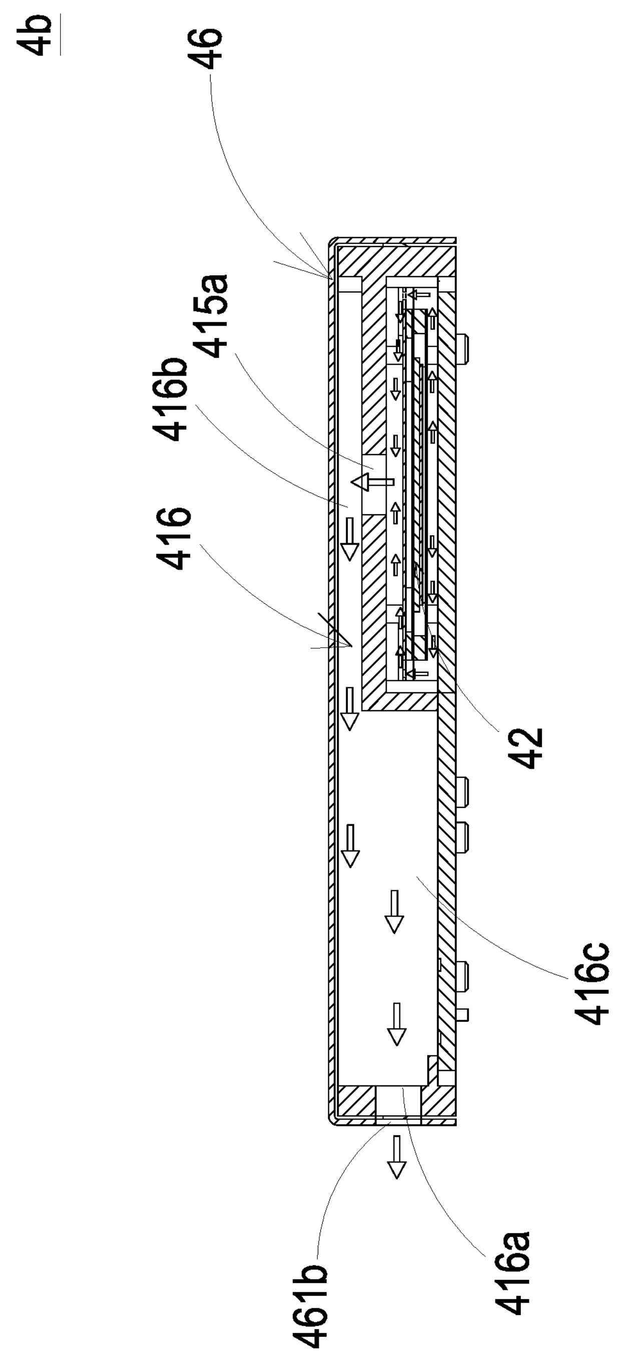

Please refer to FIGS. 6B and 6C. In the embodiment, the gas-guiding-component loading region 415 is concavely formed from the second surface 412 and in communication with the gas-inlet groove 414. A ventilation hole 415*a* penetrates a bottom surface of the gas-guiding-component loading region 415. In the embodiment, the gas-outlet groove 416 includes a gas-outlet 416*a*, and the gas-outlet 416*a* spatially corresponds to the outlet opening 461*b* of the outer cover 46. The gas-outlet groove 416 includes a first section 416*b* and a second section 416*c*. The first section 416*b* is hollowed out from the first surface 411 to the second surface 412 in a vertical projection area of the gas-guiding-component loading region 415 spatially corresponding thereto. The second section 416*c* is hollowed out from the first surface 411 to the second surface 412 in a region where the first surface 411 is not aligned with the vertical projection area of the gas-guiding-component loading region 415 and extended therefrom. The first section 416*b* and the second section 416*c* are connected to form a stepped structure. Moreover, the first section 416*b* of the gas-outlet groove 416 is in communication with the ventilation hole 415*a* of the gas-guiding-component loading region 415, and the second section 416*c* of the gas-outlet groove 416 is in communication with the gas-outlet 416*a*. In that, when first surface 411 of the base 41 is attached and covered by the outer cover 46, and the second surface 412 of the base 41 is attached and covered by the driving circuit board 43, the gas-outlet groove 416 defines an outlet path, as shown in FIGS. 11B and 11C.

Please refer to FIG. 6A and FIG. 7. In the embodiment, the laser component 44 and the particulate sensor 45 are disposed on the driving circuit board 43 and accommodated in the base 41. In order to describe the positions of the laser component 44 and the particulate sensor 45 in the base 41, the driving circuit board 43 is specifically omitted in FIG. 7 to explain clearly. Please refer to FIG. 6A, FIG. 6C, FIG. 7 and FIG. 12. In the embodiment, the laser component 44 is accommodated in the laser loading region 413 of the base 41, and the particulate sensor 45 is accommodated in the gas-inlet groove 414 of the base 41 and aligned to the laser component 44. In addition, the laser component 44 spatially corresponds to the transparent window 414*b*, a light beam emitted by the laser component 44 passes through the transparent window 414*b* and is irradiated into the gas-inlet groove 414. A light beam path emitted from the laser component 44 passes through the transparent window 414*b* and extends in a direction perpendicular to the gas-inlet groove 414, thereby forming an orthogonal direction with the gas-inlet groove 414. In the embodiment, a projecting light beam emitted from the laser component 44 passes through the transparent window 414*b* and enters the gas-inlet groove 414, and suspended particles contained in the gas passing through the gas-inlet groove 414 is irradiated by the projecting light beam. When the suspended particles contained in the gas are irradiated to generate scattered light spots, the scattered light spots are received and calculated by the particulate sensor 45 for obtaining related information about the sizes and the concentration of the suspended particles contained in the gas. In the embodiment, the particulate sensor 45 is a PM2.5 sensor.

Figure 8A:
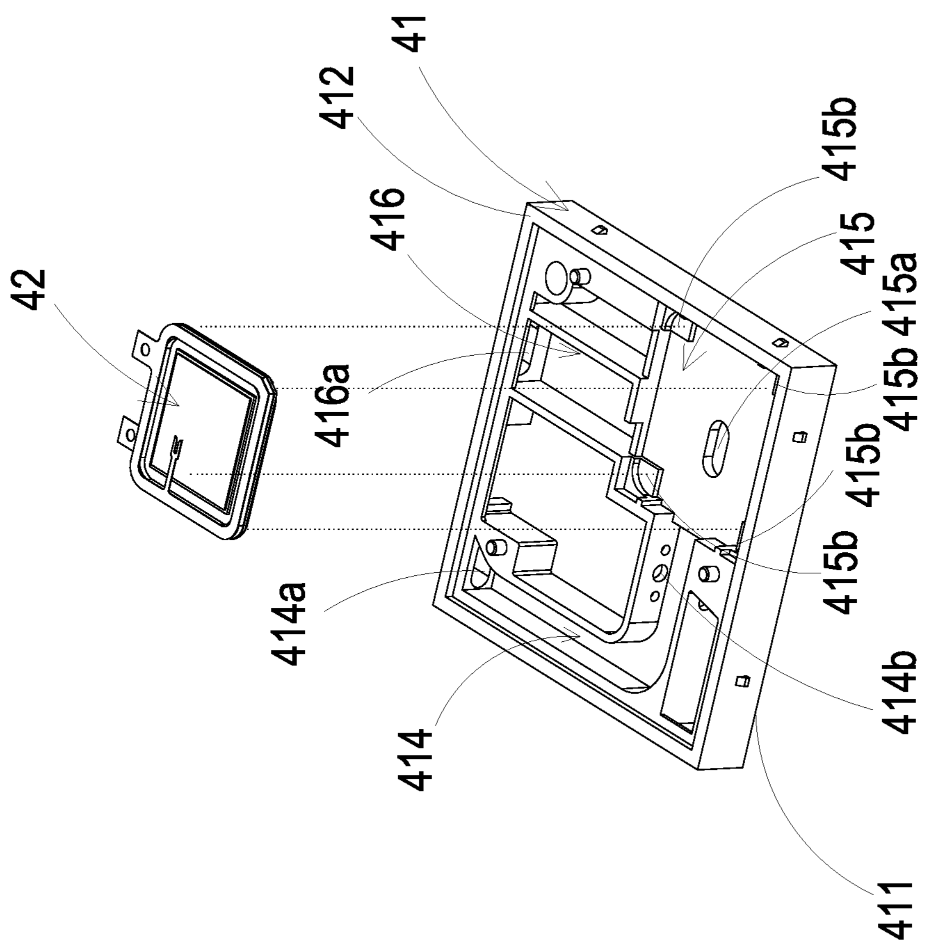
FIG. 8A is a schematic exploded view illustrating the combination of the piezoelectric actuator and the base according to the present disclosure.
Figure 8B:
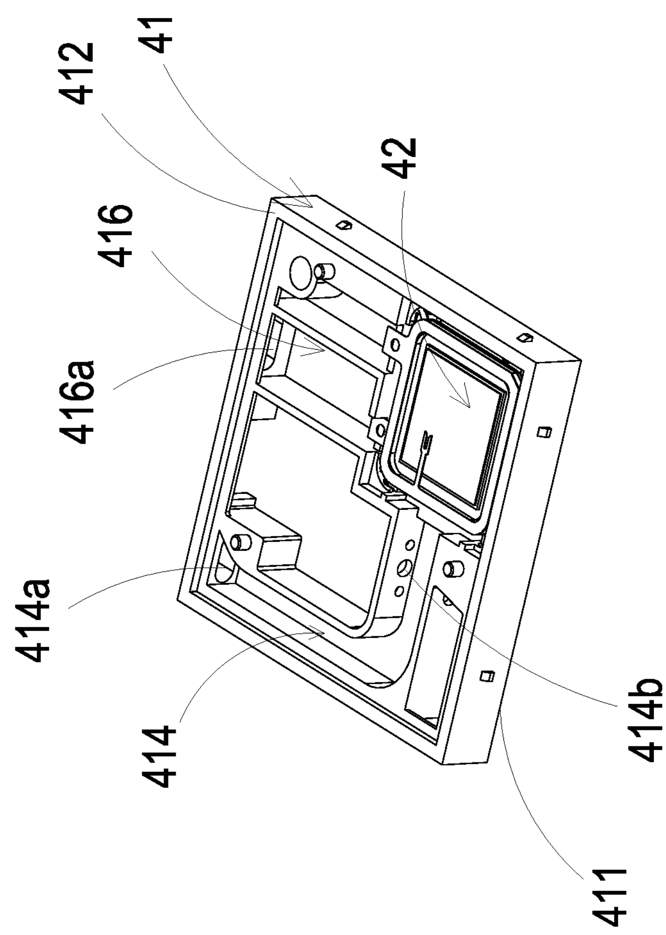
FIG. 8B is a schematic perspective view illustrating the combination of the piezoelectric actuator and the base according to the present disclosure.

Please refer to FIG. 8A and FIG. 8B. The piezoelectric actuator 42 is accommodated in the gas-guiding-component loading region 415 of the base 41. Preferably but not exclusively, the gas-guiding-component loading region 415 is square and includes four positioning protrusions 145*b* disposed at four corners of the gas-guiding-component loading region 415, respectively. The piezoelectric actuator 42 is disposed in the gas-guiding-component loading region 415 through the four positioning protrusions 415*b*. In addition, as shown in FIGS. 6A, 6B, 11B and 11C, the gas-guiding-component loading region 415 is in communication with the gas-inlet groove 414. When the piezoelectric actuator 42 is enabled, the gas in the gas-inlet groove 414 is inhaled by the piezoelectric actuator 42, so that the gas flows into the piezoelectric actuator 42. Furthermore, the gas is transported into the gas-outlet groove 416 through the ventilation hole 415*a* of the gas-guiding-component loading region 415.

Please refer to FIGS. 5A and 5B. In the embodiment, the driving circuit board 43 covers and is attached to the second surface 412 of the base 41, and the laser component 44 is positioned and disposed on the driving circuit board 43, and is electrically connected to the driving circuit board 43. The particulate sensor 45 is positioned and disposed on the driving circuit board 43, and is electrically connected to the driving circuit board 43. The outer cover 46 covers the base 41 and is attached to the first surface 411 of the base 41. Moreover, the outer cover 46 includes a side plate 461. The side plate 461 has an inlet opening 461*a* and an outlet opening 461*b*. When the outer cover 46 covers the base 41, the inlet opening 461*a* spatially corresponds to the gas-inlet 414*a* of the base 41 (as shown in FIG. 11A), and the outlet opening 461*b* spatially corresponds to the gas-outlet 416*a* of the base 41 (as shown in FIG. 11C).

Figure 9A:
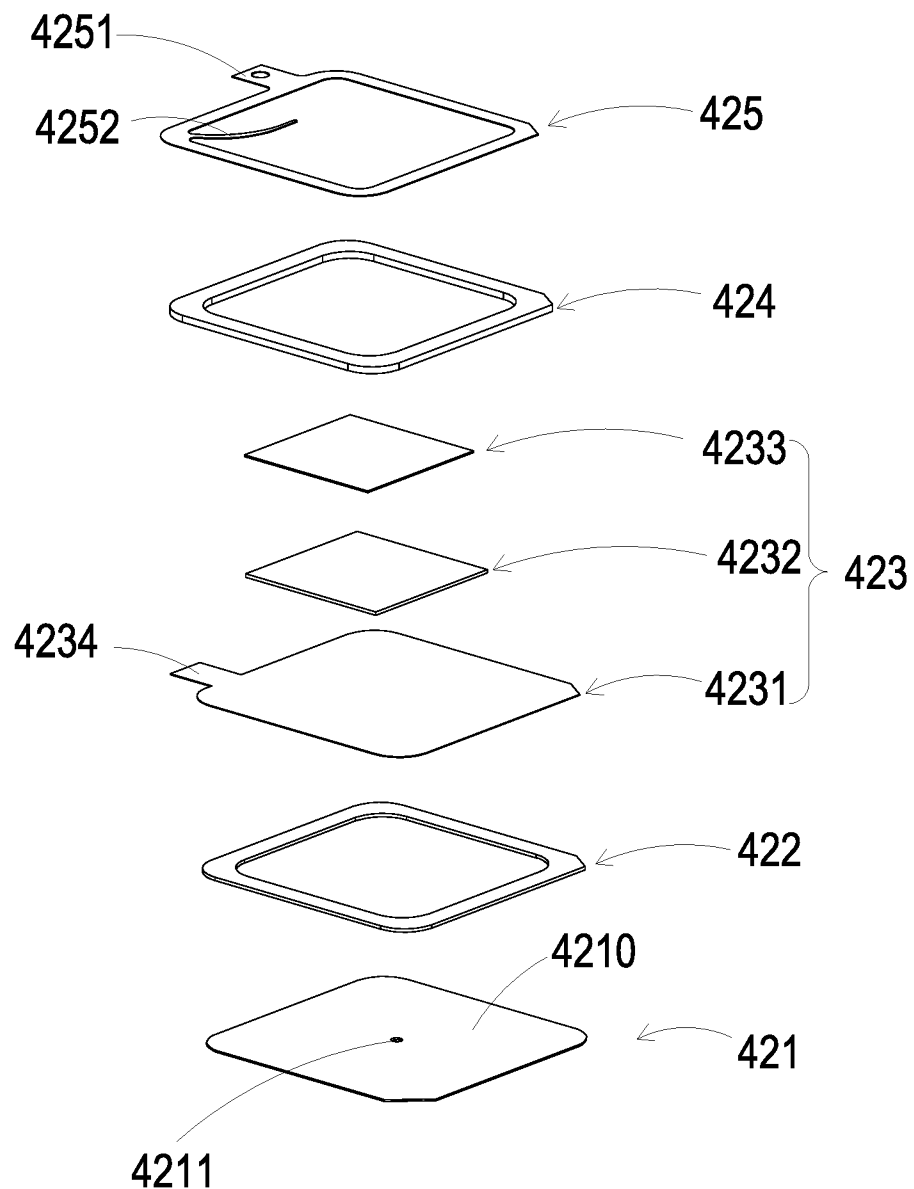
FIG. 9A is a schematic exploded view illustrating the piezoelectric actuator of the present disclosure.
Figure 9B:
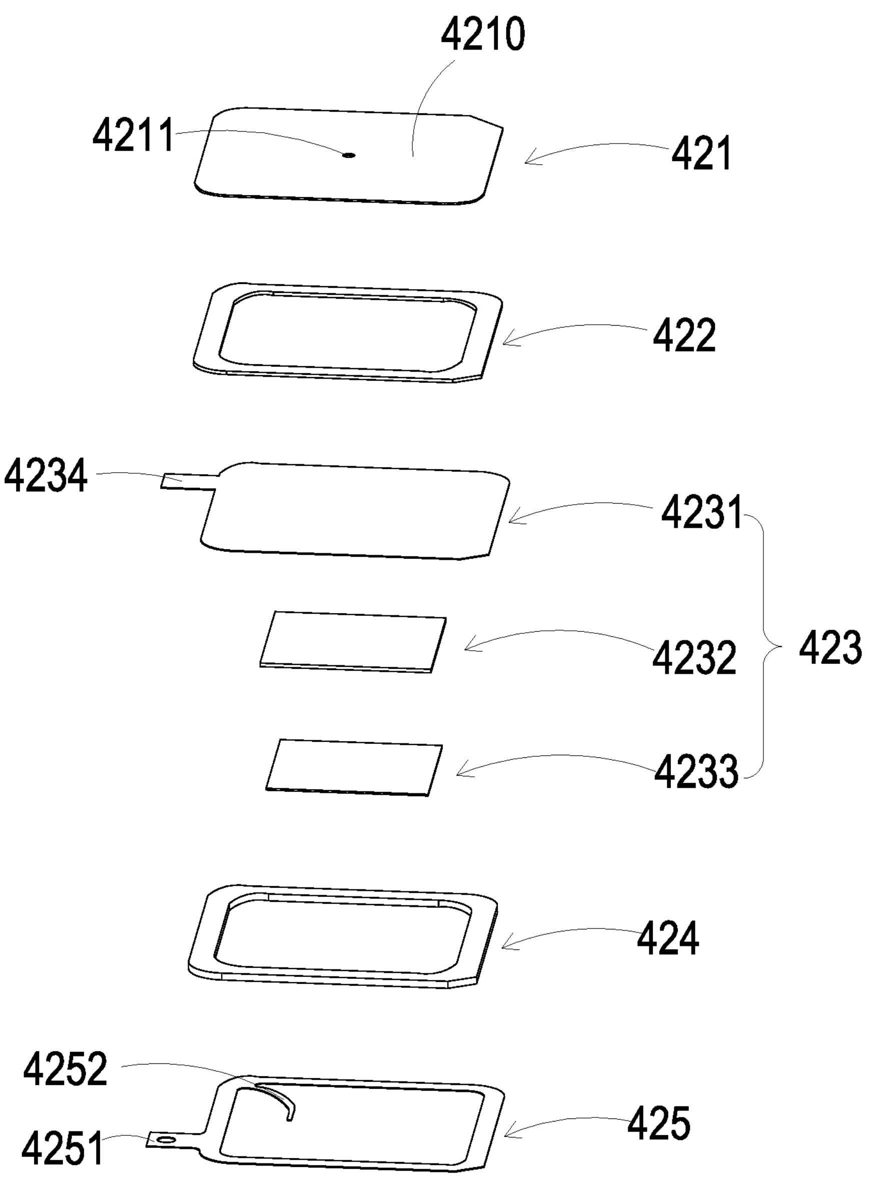
FIG. 9B is a schematic exploded view illustrating the piezoelectric actuator of the present disclosure and taken from another perspective angle.

Please refer to FIGS. 9A and 9B. In the embodiment, the piezoelectric actuator 42 includes a gas-injection plate 421, a chamber frame 422, an actuator element 423, an insulation frame 424 and a conductive frame 425. In the embodiment, the gas-injection plate 421 is made by a flexible material and includes a suspension plate 4210 and a hollow aperture 4211. The suspension plate 4210 is a sheet structure and permitted to undergo a bending deformation. Preferably but not exclusively, the shape and the size of the suspension plate 4210 are corresponding to an inner edge of the gas-guiding-component loading region 415. The shape of the suspension plate 4210 is one selected from the group consisting of a square, a circle, an ellipse, a triangle and a polygon. The hollow aperture 4211 passes through a center of the suspension plate 4210, so as to allow the gas to flow through.

In the embodiment, the chamber frame 422 is carried and stacked on the gas-injection plate 421. In addition, the shape of the chamber frame 422 is corresponding to the gas-injection plate 421. The actuator element 423 is carried and stacked on the chamber frame 422. A resonance chamber 426 is collaboratively defined by the actuator element 423, the chamber frame 422 and the suspension plate 4210 and formed among the actuator element 423, the chamber frame 422 and the suspension plate 4210. The insulation frame 424 is carried and stacked on the actuator element 423 and the appearance of the insulation frame 424 is similar to that of the chamber frame 422. The conductive frame 425 is carried and stacked on the insulation frame 424, and the appearance of the conductive frame 425 is similar to that of the insulation frame 424. In addition, the conductive frame 425 includes a conducting pin 4251 and a conducting electrode 4252. The conducting pin 4251 is extended outwardly from an outer edge of the conductive frame 425, and the conducting electrode 4252 is extended inwardly from an inner edge of the conductive frame 425. Moreover, the actuator element 423 further includes a piezoelectric carrying plate 4231, an adjusting resonance plate 4232 and a piezoelectric plate 4233. The piezoelectric carrying plate 4231 is carried and stacked on the chamber frame 422. The adjusting resonance plate 4232 is carried and stacked on the piezoelectric carrying plate 4231. The piezoelectric plate 4233 is carried and stacked on the adjusting resonance plate 4232. The adjusting resonance plate 4232 and the piezoelectric plate 4233 are accommodated in the insulation frame 424. The conducting electrode 4252 of the conductive frame 425 is electrically connected to the piezoelectric plate 4233. In the embodiment, the piezoelectric carrying plate 4231 and the adjusting resonance plate 4232 are made by a conductive material. The piezoelectric carrying plate 4231 includes a piezoelectric pin 4234. The piezoelectric pin 4234 and the conducting pin 4251 are electrically connected to a driving circuit (not shown) of the driving circuit board 43, so as to receive a driving signal, such as a driving frequency and a driving voltage. In that, a loop is formed by the piezoelectric pin 4234, the piezoelectric carrying plate 4231, the adjusting resonance plate 4232, the piezoelectric plate 4233, the conducting electrode 4252, the conductive frame 425 and the conducting pin 4251 for the driving signal. Moreover, the insulation frame 424 is insulated between the conductive frame 425 and the actuator element 423, so as to avoid the occurrence of a short circuit. Thereby, the driving signal is transmitted to the piezoelectric plate 4233. After receiving the driving signal such as the driving frequency and the driving voltage, the piezoelectric plate 4233 deforms due to the piezoelectric effect, and the piezoelectric carrying plate 4231 and the adjusting resonance plate 4232 are further driven to generate the bending deformation in the reciprocating manner.

As described above, the adjusting resonance plate 4232 is located between the piezoelectric plate 4233 and the piezoelectric carrying plate 4231 and served as a buffer between the piezoelectric plate 4233 and the piezoelectric carrying plate 4231. Thereby, the vibration frequency of the piezoelectric carrying plate 4231 is adjustable. Basically, the thickness of the adjusting resonance plate 4232 is greater than the thickness of the piezoelectric carrying plate 4231, and the thickness of the adjusting resonance plate 4232 is adjustable, thereby adjusting the vibration frequency of the actuator element 423.

Please refer to FIGS. 9A to 9C and FIG. 10A. In the embodiment, the gas-injection plate 421, the chamber frame 422, the actuator element 423, the insulation frame 424 and the conductive frame 425 are stacked and positioned in the gas-guiding-component loading region 415 sequentially, so that the piezoelectric actuator 42 is supported and positioned in the gas-guiding-component loading region 415. The bottom of the gas-injection plate 421 is fixed on the four positioning protrusions 415*b* of the gas-guiding-component loading region 415 for supporting and positioning, so that the suspension plate 4210 of the gas-injection plate 421 and an inner edge of the gas-guiding-component loading region 415 define a plurality of vacant spaces 4212 in the piezoelectric actuator 42 for gas flowing.

Figure 10A:
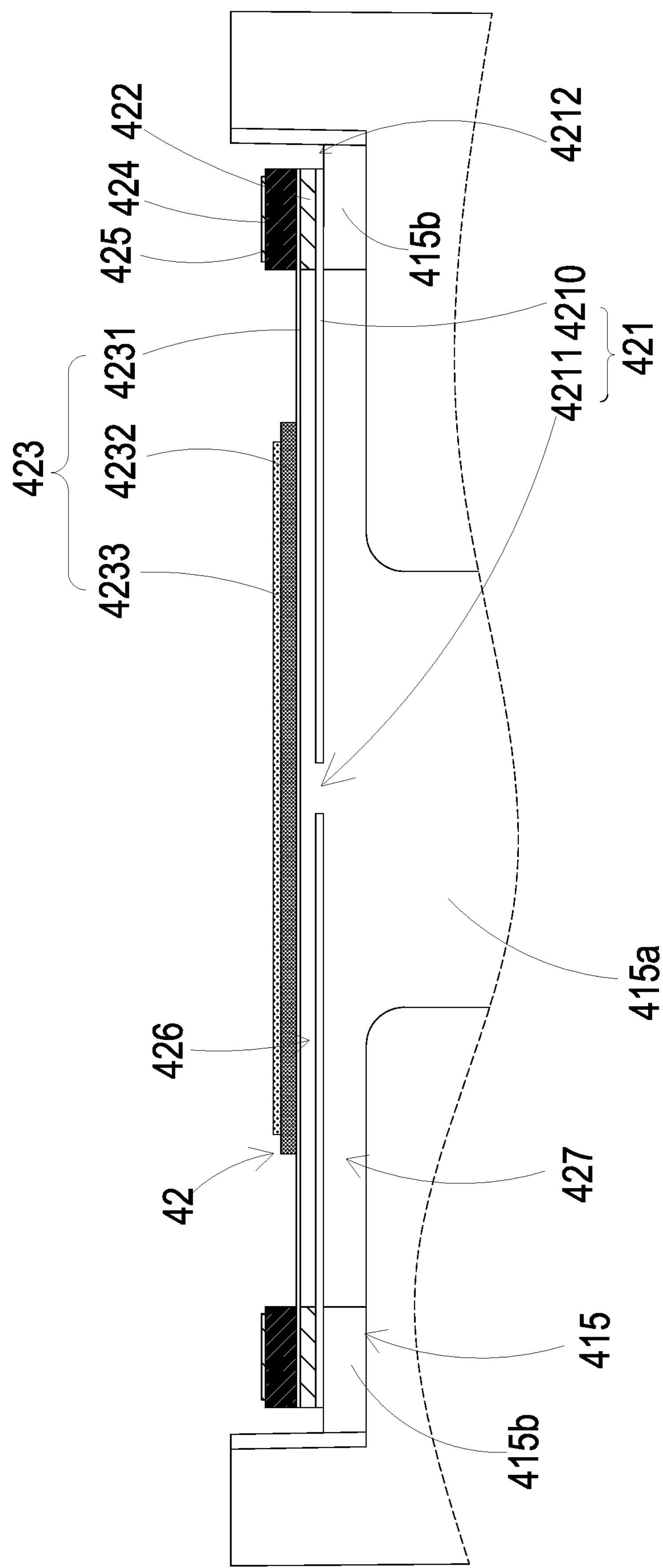
FIG. 10A is a schematic cross-sectional view illustrating the piezoelectric actuator accommodated in the gas-guiding-component loading region according to the present disclosure.

Please refer to FIG. 10A. A flowing chamber 427 is formed between the gas-injection plate 421 and the bottom surface of the gas-guiding-component loading region 415. The flowing chamber 427 is in communication with the resonance chamber 426 among the actuator element 423, the chamber frame 422 and the suspension plate 4210 through the hollow aperture 4211 of the gas-injection plate 421. By controlling the vibration frequency of the gas in the resonance chamber 426 to be close to the vibration frequency of the suspension plate 4210, the Helmholtz resonance effect is generated between the resonance chamber 426 and the suspension plate 4210, and thereby the efficiency of gas transportation is improved.

Figure 10B:
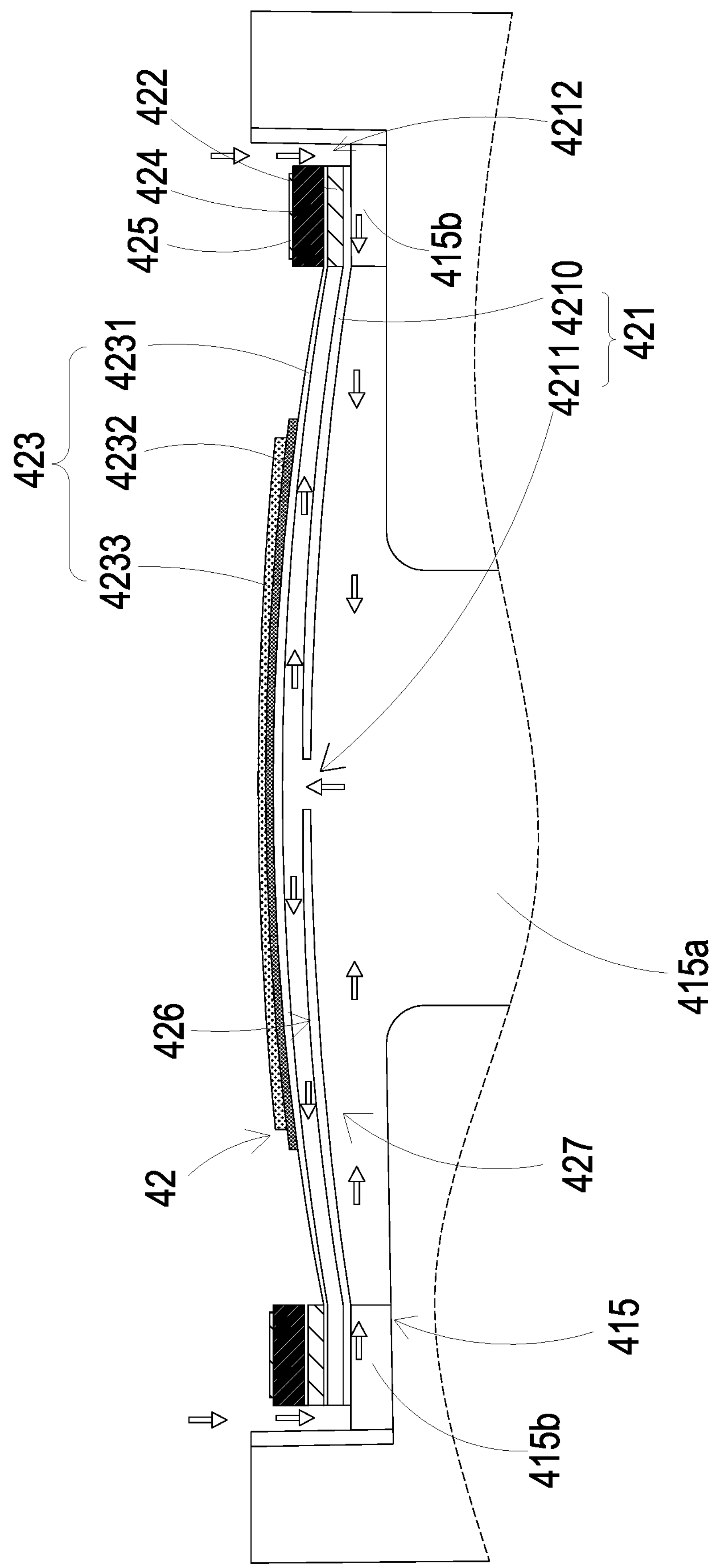
FIGS. 10B and 10C schematically illustrate the actions of the piezoelectric actuator of FIG. 10A.
Figure 10C:
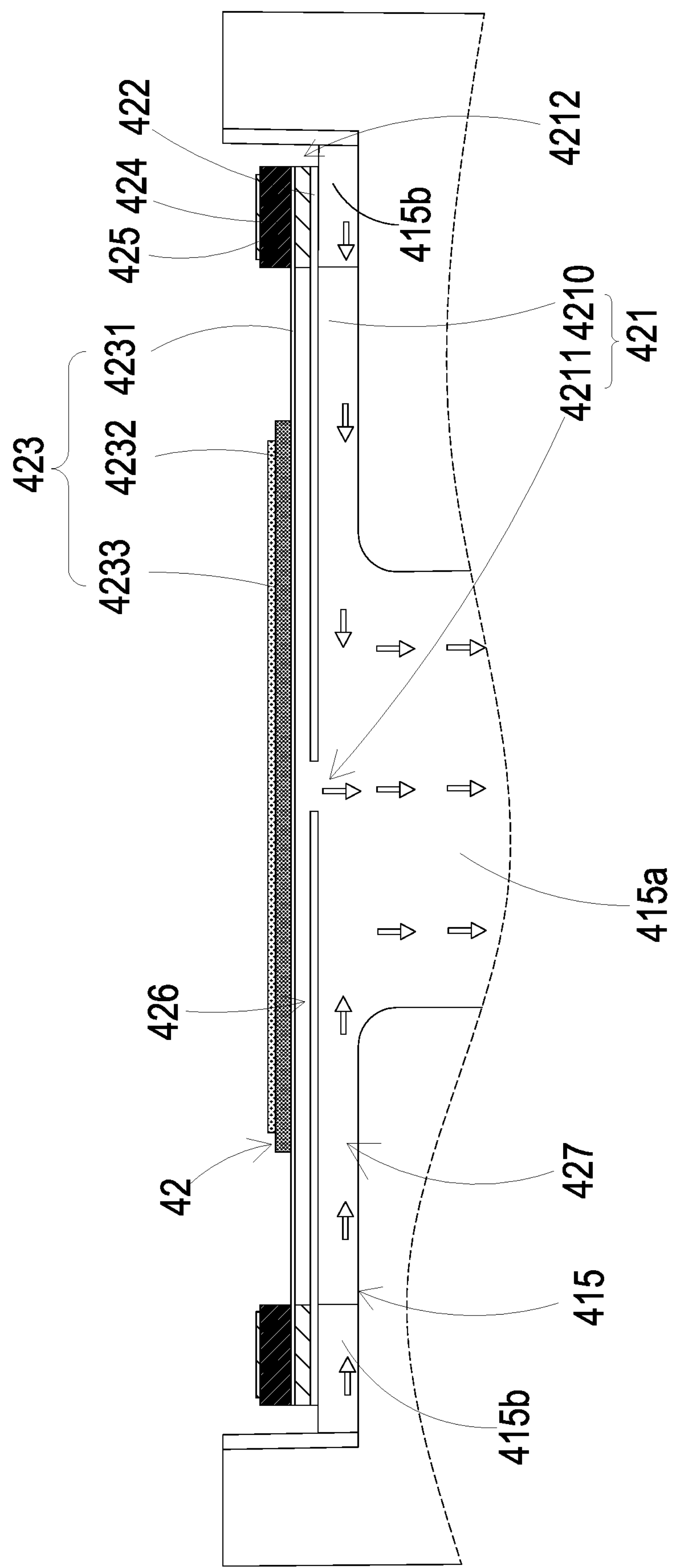

FIGS. 10B and 10C schematically illustrate the actions of the piezoelectric actuator of FIG. 10A. Please refer to FIG. 10B. When the piezoelectric plate 4233 is moved away from the bottom surface of the gas-guiding-component loading region 415, the suspension plate 4210 of the gas-injection plate 421 is driven to move away from the bottom surface of the gas-guiding-component loading region 415 by the piezoelectric plate 4233. In that, the volume of the flowing chamber 427 is expanded rapidly, the internal pressure of the flowing chamber 427 is decreased to form a negative pressure, and the gas outside the piezoelectric actuator 42 is inhaled through the vacant spaces 4212 and enters the resonance chamber 426 through the hollow aperture 4211. Consequently, the pressure in the resonance chamber 426 is increased to generate a pressure gradient. Further as shown in FIG. 10C, when the suspension plate 4210 of the gas-injection plate 421 is driven by the piezoelectric plate 4233 to move towards the bottom surface of the gas-guiding-component loading region 415, the gas in the resonance chamber 426 is discharged out rapidly through the hollow aperture 4211, and the gas in the flowing chamber 427 is compressed. In that, the converged gas close to an ideal gas state of the Benulli's law is quickly and massively ejected out of the flowing chamber 427, and transported to the ventilation hole 415*a* of the gas-guiding-component loading region 415. By repeating the above actions shown in FIG. 10B and FIG. 10C, the piezoelectric plate 4233 is driven to generate the bending deformation in a reciprocating manner. According to the principle of inertia, since the gas pressure inside the resonance chamber 426 after exhausting is lower than the equilibrium gas pressure, the gas is introduced into the resonance chamber 426 again. Moreover, the vibration frequency of the gas in the resonance chamber 426 is controlled to be close to the vibration frequency of the piezoelectric plate 4233, so as to generate the Helmholtz resonance effect to achieve the gas transportation at high speed and in large quantities.

Please refer to FIGS. 11A to 11C. FIGS. 11A to 11C schematically illustrate gas flowing paths of the gas detection main part 4*b*. Firstly, as shown in FIG. 11A, the gas is inhaled through the inlet opening 461*a* of the outer cover 46, flows into the gas-inlet groove 414 of the base 41 through the gas-inlet 414*a*, and is transported to the position of the particulate sensor 45. Further as shown in FIG. 11B, the piezoelectric actuator 42 is enabled continuously to inhale the gas in the inlet path, and it facilitates the gas to be introduced rapidly, flow stably, and be transported above the particulate sensor 45. At this time, a projecting light beam emitted from the laser component 44 passes through the transparent window 414*b* to irritate the suspended particles contained in the gas flowing above the particulate sensor 45 in the gas-inlet groove 414. When the suspended particles contained in the gas are irradiated to generate scattered light spots, the scattered light spots are received and calculated by the particulate sensor 45 for obtaining related information about the sizes and the concentration of the suspended particles contained in the gas. Moreover, the gas above the particle sensor 45 is continuously driven and transported by the piezoelectric actuator 42, flows into the ventilation hole 415*a* of the gas-guiding-component loading region 415, and is transported to the first section 416*b* of the gas-outlet groove 416. As shown in FIG. 11C, after the gas flows into the first section 416*b* of the gas-outlet groove 416, the gas is continuously transported into the first section 416*b* by the piezoelectric actuator 42, and the gas in the first section 416*b* is pushed to the second section 416*c*. Finally, the gas is discharged out through the gas-outlet 416*a* and the outlet opening 461*b*.

Figure 12:
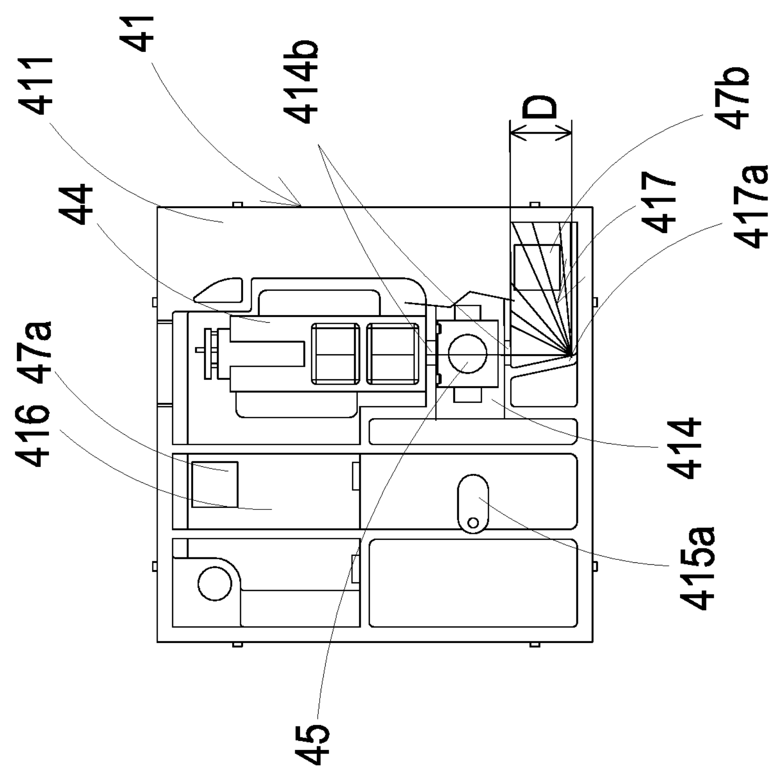
FIG. 12 schematically illustrates a light beam path emitted from the laser component of the gas detection main body of the present disclosure.

As shown in FIG. 12, the base 41 further includes a light trapping region 417. The light trapping region 417 is hollowed out from the first surface 411 to the second surface 412 and spatially corresponds to the laser loading region 413. In the embodiment, the light trapping region 417 is corresponding to the transparent window 414*b* so that the light beam emitted by the laser component 44 is projected into the light trapping region 417. The light trapping region 417 includes a light trapping structure 417*a* having an oblique cone surface. The light trapping structure 417*a* spatially corresponds to the light beam path emitted from the laser component 44. In addition, the projecting light beam emitted from the laser component 44 is reflected into the light trapping region 417 through the oblique cone surface of the light trapping structure 417*a*. It prevents the projecting light beam from being reflected to the position of the particulate sensor 45. In the embodiment, a light trapping distance D is maintained between the transparent window 414*b* and a position where the light trapping structure 417*a* receives the projecting light beam. Preferably but not exclusively, the light trapping distance D is greater than 3 mm. When the light trapping distance D is less than 3 mm, the projecting light beam projected on the light trapping structure 417*a* is easy to be reflected back to the position of the particulate sensor 45 directly due to excessive stray light generated after reflection, and it results in distortion of detection accuracy.

Please refer to FIG. 6A and FIG. 12. The gas detection main part 4*b* of the present disclosure is not only utilized to detect the suspended particles in the gas, but also further utilized to detect the characteristics of the introduced gas. Preferably but not exclusively, the gas is at least one selected from the group consisting of formaldehyde, ammonia, carbon monoxide, carbon dioxide, oxygen, ozone and a combination thereof. In the embodiment, the gas detection main part 4*b* further includes a first volatile-organic-compound sensor 47*a*. The first volatile-organic-compound sensor 47*a* is positioned and disposed on the driving circuit board 43, electrically connected to the driving circuit board 43, and accommodated in the gas-outlet groove 416, so as to detect the gas flowing through the outlet path of the gas-outlet groove 416. Thus, the concentration or the characteristics of volatile organic compounds contained in the gas in the outlet path is detected. Alternatively, in an embodiment, the gas detection main part 4*b* further includes a second volatile-organic-compound sensor 47*b*. The second volatile-organic-compound sensor 47*b* is positioned and disposed on the driving circuit board 43, and electrically connected to the driving circuit board 43. In the embodiment, the second volatile-organic-compound sensor 47*b* is accommodated in the light trapping region 417. Thus, the concentration or the characteristics of volatile organic compounds contained in the gas flowing through the inlet path of the gas-inlet groove 414 and transported into the light trapping region 417 through the transparent window 414*b* is detected.

In summary, the present disclosure provides a gas detection purification device. With an external pluggable or detachable gas detection module embedded in the gas purification device, air quality around the gas purification device is detected at any time, and information of the air quality is transmitted to an external device in real time to obtain gas detection information and an alarm notice. It prevents the hazardous gas exposed in the environment from affecting the human health and causing the harm. Furthermore, the gas purification device is utilized to provide the benefits of purifying the air quality. The present disclosure includes the industrial applicability and the inventive steps.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A gas detection purification device, comprising:

a main body comprising at least one inlet, at least one outlet, a gas-flow channel and an external socket, wherein the gas-flow channel is disposed between the at least one inlet and the at least one outlet;

a purification unit disposed in the gas-flow channel for filtering gas introduced through the gas-flow channel;

a gas guider disposed in the gas-flow channel and located at a side of the purification unit, wherein the gas is inhaled through the at least one inlet, flows through the purification unit for filtration and purification, and is discharged out through the at least one outlet;

a gas detection module plugged into the external socket and integrally connected to the main body as one piece, or detached from the external socket and separated from the main body; and a controlling-driving module disposed within the main body, allowing to be electrically connected by the gas guider to control operations of the gas guider in an enabled state and a disabled state, and comprising a connection port, which allows the gas detection module to be inserted and driven in an electrical connection, so that the gas detection module detects the gas outside the main body to obtain a gas detection datum, and the gas detection datum is outputted to the controlling-driving module to control the operations of the gas guider in the enabled state and the disabled state, wherein the gas detection module comprises:

a housing comprising at least one gas inlet and at least one gas outlet;

a gas detection main part disposed within the housing and in communication with the at least one gas inlet and the at least one gas outlet of the housing for detecting the gas introduced from the outside of the housing to obtain the gas detection datum;

a control circuit unit comprising a microprocessor, a communicator and a power module packaged into one piece in electrical connection; and an external connection device, disposed on the control circuit unit and packaged into one piece in electrical connection;

wherein the gas detection main part, the control circuit unit and the external connection device are covered by the housing for protection, wherein the external connection device is exposed out of the housing for correspondingly connecting to the connection port of the controlling-driving module, so that the gas detection module is in electrical connection, the gas detection main part is actuated to detect the gas outside the main body to generate a gas detection signal, which is received, calculated, processed and converted into the gas detection datum by the microprocessor, and the gas detection datum is outputted to the controlling-driving module to control the operations of the gas guider in the enabled state and the disabled state.

2. The gas detection purification device according to claim 1, wherein the purification unit is a filter unit comprising a filter screen, wherein the gas introduced is filtered through the filter screen for filtration and purification.

3. The gas detection purification device according to claim 2, wherein the filter screen is one selected from the group consisting of an electrostatic filter screen, an activated carbon filter screen and a high efficiency particulate air filter screen.

4. The gas detection purification device according to claim 1, wherein the purification unit is a photo-catalyst unit comprising a photo-catalyst and an ultraviolet lamp, and the photo-catalyst is irradiated with the ultraviolet lamp to purify the gas.

5. The gas detection purification device according to claim 1, wherein the purification unit is a photo-plasma unit comprising a nanometer irradiation tube, wherein the gas containing volatile formaldehyde, toluene and volatile organic gases is irradiated by the nanometer irradiation tube, whereby the gas is purified.

6. The gas detection purification device according to claim 1, wherein the purification unit is a negative ionizer comprising at least one electrode wire, at least one dust collecting plate and a boost power supply, wherein when a high voltage is discharged through the electrode wire, particles contained in the gas introduced are positively charged and attached to the dust collecting plate negatively charged, whereby the gas is purified.

7. The gas detection purification device according to claim 1, wherein the purification unit is a plasma ion unit comprising an upper electric-field protection screen, a high efficiency particulate air filter screen, a high-voltage discharge electrode, a lower electric-field protection screen and a boost power supply device, wherein the boot power supply device provides a high voltage to the high-voltage discharge electrode to discharge to form a high-voltage plasma column with plasma ion, and the gas is purified by the plasma ion.

8. The gas detection purification device according to claim 1, wherein the gas guider is a fan.

9. The gas detection purification device according to claim 1, wherein the gas guider is an actuating pump.

10. The gas detection purification according to claim 9, wherein the actuating pump comprises:

a gas inlet plate having at least one gas inlet aperture, at least one convergence channel, and a convergence chamber, wherein the at least one gas inlet aperture is disposed to inhale the gas, the at least one gas inlet aperture correspondingly penetrates through the at least one convergence channel, and the at least one convergence channel is converged into the convergence chamber, so that the gas inhaled through the at least one gas inlet aperture is converged into the convergence chamber;

a resonance plate disposed on the gas inlet plate and having a central aperture, a movable part and a fixed part, wherein the central aperture is disposed at a center of the resonance plate, and corresponds in position to the convergence chamber of the gas inlet plate, the movable part surrounds the central aperture and corresponds in position to the convergence chamber, and the fixed part surrounds the movable part and is fixedly attached on the gas inlet plate; and a piezoelectric actuator correspondingly disposed on the resonance plate and comprising:

a first insulation plate;

a conductive plate; and a second insulation plate wherein, the gas inlet plate, the resonance plate, the piezoelectric actuator, the first insulation plate, the conductive plate and the second insulation plate are stacked sequentially, and a chamber space is formed between the resonance plate and the piezoelectric actuator, so that when the piezoelectric actuator is driven, the gas introduced from the at least one gas inlet aperture of the gas inlet plate is converged to the convergence chamber through the at least one convergence channel, and flows through the central aperture of the resonance plate so as to produce a resonance by the movable part of the resonance plate and the piezoelectric actuator to transport the gas.

11. The gas detection purification device according to claim 10, wherein the piezoelectric actuator comprises:

a suspension plate being square-shaped and being permitted to undergo a bending vibration;

an outer frame surrounding the suspension plate;

at least one bracket connected between the suspension plate and the outer frame to provide an elastic support for the suspension plate, wherein a surface of the suspension plate and a surface of the outer frame are non-coplanar, and a chamber space is formed between a surface of the suspension plate and the resonance plate, and a piezoelectric element having a side, wherein a length of the side of the piezoelectric element is less than or equal to that of the suspension plate, and the piezoelectric element is attached on a surface of the suspension plate, wherein when a voltage is applied to the piezoelectric element, the suspension plate is driven to undergo the bending vibration.

12. The gas detection purification device according to claim claim 1, wherein the gas detection main part comprises:

a base comprising:

a first surface;

a second surface opposite to the first surface;

a laser loading region hollowed out from the first surface to the second surface;

a gas-inlet groove concavely formed from the second surface and disposed adjacent to the laser loading region, wherein the gas-inlet groove comprises a gas-inlet and two lateral walls, the gas-inlet is in communication with an environment outside the base, and a transparent window is opened on the two lateral walls and is in communication with the laser loading region;

a gas-guiding-component loading region concavely formed from the second surface and in communication with the gas-inlet groove, wherein a ventilation hole penetrates a bottom surface of the gas-guiding-component loading region, and the gas-guiding-component loading region has four positioning protrusions disposed at four corners thereof; and a gas-outlet groove concavely formed from the first surface, spatially corresponding to the bottom surface of the gas-guiding-component loading region, and hollowed out from the first surface to the second surface in a region where the first surface is not aligned with the gas-guiding-component loading region, wherein the gas-outlet groove is in communication with the ventilation hole, and a gas-outlet is disposed in the gas-outlet groove and in communication with the environment outside the base;

a piezoelectric actuator accommodated in the gas-guiding-component loading region;

a driving circuit board covering and attached to the second surface of the base;

a laser component positioned and disposed on the driving circuit board, electrically connected to the driving circuit board, and accommodated in the laser loading region, wherein a light beam path emitted from the laser component passes through the transparent window and extends in a direction perpendicular to the gas-inlet groove, thereby forming an orthogonal direction with the gas-inlet groove;

a particulate sensor positioned and disposed on the driving circuit board, electrically connected to the driving circuit board, and disposed at an orthogonal position where the gas-inlet groove intersects the light beam path of the laser component in the orthogonal direction, so that suspended particles passing through the gas-inlet groove and irradiated by a projecting light beam emitted from the laser component are detected; and an outer cover covering the first surface of the base and comprising a side plate, wherein the side plate has an inlet opening spatially corresponding to the gas-inlet and an outlet opening spatially corresponding to the gas-outlet, respectively, wherein the first surface of the base is covered with the outer cover, and the second surface of the base is covered with the driving circuit board, so that an inlet path is defined by the gas-inlet groove, and an outlet path is defined by the gas-outlet groove, so that the gas is inhaled from the environment outside the base by the piezoelectric actuator, transported into the inlet path defined by the gas-inlet groove through the inlet opening, and passes through the particulate sensor to detect the concentration of the suspended particles contained in the gas, and the gas transported through the piezoelectric actuator is transported out of the outlet path defined by the gas-outlet groove through the ventilation hole and then discharged through the outlet opening.

13. The gas detection purification device according to claim 12, wherein the base comprises a light trapping region hollowed out from the first surface to the second surface and spatially corresponding to the laser loading region, wherein the light trapping region comprises a light trapping structure having an oblique cone surface and spatially corresponding to the light beam path, wherein a light trapping distance is maintained between the transparent window and a position where the light trapping structure receives the projecting light beam, wherein the light trapping distance is greater than 3 mm.

14. The gas detection purification device according to claim 13, further comprising a second volatile-organic-compound sensor positioned and disposed on the driving circuit board, electrically connected to the driving circuit board, and accommodated in the light trapping region, so as to detect the gas flowing through the inlet path of the gas-inlet groove and transported into the light trapping region through the transparent window.

15. The gas detection purification device according to claim 12, wherein the particulate sensor is a PM2.5 sensor.

16. The gas detection purification device according to claim 12, wherein the piezoelectric actuator comprises:

a gas-injection plate comprising a suspension plate and a hollow aperture, wherein the suspension plate is permitted to undergo a bending deformation, and the hollow aperture is formed at a center of the suspension plate;

a chamber frame carried and stacked on the suspension plate;

an actuator element carried and stacked on the chamber frame for being driven in response to an applied voltage to undergo the bending deformation in a reciprocating manner, wherein the actuator element comprises:

a piezoelectric carrying plate carried and stacked on the chamber frame;

an adjusting resonance plate carried and stacked on the piezoelectric carrying plate; and a piezoelectric plate carried and stacked on the adjusting resonance plate, wherein the piezoelectric plate is configured to drive the piezoelectric carrying plate and the adjusting resonance plate to generate the bending deformation in the reciprocating manner by the applied voltage;

an insulation frame carried and stacked on the actuator element; and a conductive frame carried and stacked on the insulation frame, wherein the gas-injection plate is fixed on the four positioning protrusions of the gas-guiding-component loading region for supporting and positioning, so that the gas-injection plate and an inner edge of the gas-guiding-component loading region define a vacant space for gas flowing, a flowing chamber is formed between the gas-injection plate and the bottom surface of the gas-guiding-component loading region, a resonance chamber is formed among the actuator element, the chamber frame and the suspension plate, wherein when the actuator element is enabled to drive the gas-injection plate to move in resonance, the suspension plate of the gas-injection plate is driven to generate the bending deformation in a reciprocating manner, the gas is inhaled through the vacant space, flows into the flowing chamber, and is discharged out, so as to achieve gas transportation.

17. The gas detection purification device according to claim 12, further comprising a first volatile-organic-compound sensor positioned and disposed on the driving circuit board, electrically connected to the driving circuit board, and accommodated in the gas-outlet groove, so as to detect the gas flowing through the outlet path of the gas-outlet groove.

18. The gas detection purification device according to claim 12, the gas detection signal is received, calculated, processed and converted into the gas detection datum by the microprocessor, and the gas detection datum outputted from the microprocessor is received and outputted by the communicator, and further externally transmitted to an external device through a communication transmission for storing, so that the external device generates gas detection information and an alarm notice, wherein the communication transmission is a wire communication transmission or a wireless communication transmission, the wire communication transmission is a USB transmission, and the wireless communication transmission is one selected from the group consisting of Wi-Fi transmission, a radio frequency identification transmission, Bluetooth transmission and a near field communication (NFC) transmission, wherein the external device is one selected from the group consisting of a cloud system, a portable device and a computer system.

* * * * *